US009102920B2

(12) United States Patent
Feng et al.

(10) Patent No.: US 9,102,920 B2
(45) Date of Patent: Aug. 11, 2015

(54) METHOD OF EFFECTING DE-DIFFERENTIATION OF A CELL

(75) Inventors: Bo Feng, Singapore (SG); Jianming Jiang, Singapore (SG); Huck Hui Ng, Singapore (SG); Thomas Lufkin, Singapore (SG); Petra Kraus, Singapore (SG)

(73) Assignee: Agency for Science, Technology and Research, Connexis (SG)

( * ) Notice: Subject to any disclaimer, the term of this patent is extended or adjusted under 35 U.S.C. 154(b) by 0 days.

(21) Appl. No.: 12/991,284

(22) PCT Filed: Oct. 21, 2008

(86) PCT No.: PCT/SG2008/000407
§ 371 (c)(1),
(2), (4) Date: Mar. 16, 2011

(87) PCT Pub. No.: WO2009/136867
PCT Pub. Date: Nov. 12, 2009

(65) Prior Publication Data
US 2011/0165570 A1    Jul. 7, 2011

Related U.S. Application Data

(60) Provisional application No. 61/050,726, filed on May 6, 2008.

(51) Int. Cl.
*C12N 5/074* (2010.01)

(52) U.S. Cl.
CPC .......... *C12N 5/0696* (2013.01); *C12N 2501/38* (2013.01); *C12N 2501/602* (2013.01); *C12N 2501/603* (2013.01); *C12N 2501/606* (2013.01); *C12N 2510/00* (2013.01)

(58) Field of Classification Search
CPC ............................... C12N 5/0696; C12N 5/38
See application file for complete search history.

(56) References Cited

U.S. PATENT DOCUMENTS

| 5,843,780 | A | 12/1998 | Thomson |
| 6,090,622 | A | 7/2000 | Gearhart et al. |
| 7,964,401 | B2 | 6/2011 | Yamanaka |
| 2006/0189825 | A1 | 8/2006 | Forman et al. |
| 2008/0076176 | A1 | 3/2008 | Dominko et al. |
| 2009/0068742 | A1 | 3/2009 | Yamanaka |

FOREIGN PATENT DOCUMENTS

| WO | WO 96/23879 A1 | 8/1996 |
| WO | WO 01/04144 A2 | 1/2001 |
| WO | WO 02/080888 A2 | 10/2002 |
| WO | WO 03/029462 A1 | 4/2003 |
| WO | WO 2005/019254 A1 | 3/2005 |
| WO | WO 2005/019255 A1 | 3/2005 |
| WO | WO 2005/019256 A2 | 3/2005 |
| WO | WO 2008/021483 A2 | 2/2008 |
| WO | WO 2008/103462 A2 | 8/2008 |
| WO | WO 2009/157593 A1 | 12/2009 |

OTHER PUBLICATIONS

Yamanaka et al. Cell Stem Cell 1:39-49, 2007.*
Jaenisch et al. Cell 132:567-582, 2008.*
Abad, M. et al., *Structural Determination of Estrogen-Related Receptor γ in the Presence of Phenol Derivative Compunds*, Journal of Steroid Biochemistry & Molecular Biology, 108, (2008), pp. 44-54.
Ami, D. et al., *Embryonic Stem Cell Differentiation Studied by FT-IR Spectroscopy*, Biochemica et Biophysica Acta, 1783, (2008), pp. 98-106.
Ao, A. et al., *Involvement of Estrogen-Related Receptors in Transcriptional Response to Hypoxia and Growth of Solid Tumors*, PNSA, vol. 105, No. 22, (2008), pp. 7821-7826.
Aoi, T. et al., *Generation of Pluripotent Stem Cells From Adult Mouse Liver and Stomach Cells*, Science, vol. 321, (2008), pp. 699-702, 1-2.
Bernstein, B. E. et al., *A Bivalent Chromatin Structure Marks Key Developmental Genes in Embryonic Stem Cells*, Cells, 125, (2006), pp. 315-326.
Beste, G. et al., *Small Antibody-like Proteins With Prescribed Ligand Specificities Derived From the Lipocalin Fold*, Proc. Natl. Acad. Sci. USA, vol. 96, (1999), pp. 1898-1903.
Blelloch, R. et al., *Generation of Induced Pluripotent Stem Cells in the Absence of Drug Selection*, Cell Stem Cell, 1, (2007), pp. 245-247.
Boiani, M. et al., *Regulatory Networks in Embryo-Derived Pluripotent Stem Cells*, Nature Reviews, Molecular Cell Biology, vol. 6, (2005), pp. 872-884.
Bonnelye, E. et al., *Expression of the Estrogen-Related Receptor 1 (EER-1) Orphan Receptor Mouse Development*, Mechanisms of Development, 65, (1997), pp. 71-85.
Brambrink, T. et al., *Sequential Expression of Pluripotency Markers During Direct Reprogramming of Mouse Somatic Cells*, Cell Stem Cell, 2, (2008), pp. 151-159.
Bunnell, B. A. et al., *Adipose-Derived Stem Cells: Isolation, Expansion and Differentiation*, Methods, 45, (2008), pp. 115-120.
Carter, M. G. et al., *An in situ Hybridization-based Screen for Heterogeneously Expressed Genes in Mouse ES Cells*, Gene Expression Patterns, 8, (2008), pp. 181-198.
Cartwright, P. et al., *LIF/STAT3 Controls ES Cell Self-Renewal and Pluripotency by a Myc-dependent Mechanism*, Research Article, Development, 132, 5, (2005), pp. 885-896.
Chen, X. et al., *Intergration of External Signaling Pathways With the Core Transcriptional Network in Embryonic Stem Cells*, Cell, 133, (2008), pp. 1106-1117.
Chojnacki, A. et al., *Production of Neurons, Astrocytes, and Oligodendrocytes from Mammalian CNS Stem Ceells*, Nature Protocols, vol. 3, No. 6, (2008), pp. 935-940.

(Continued)

*Primary Examiner* — Marcia S Noble
(74) *Attorney, Agent, or Firm* — Alston & Bird LLP

(57) ABSTRACT

The invention provides a method of effecting de-differentiation of an at least partially differentiated cell or of maintaining pluripotency and/or self-renewing characteristics of an undifferentiated cell. The method comprises increasing the amount or the activity of an Err protein, or a functional fragment thereof, in the cell.

17 Claims, 20 Drawing Sheets
(14 of 20 Drawing Sheet(s) Filed in Color)

(56) References Cited

OTHER PUBLICATIONS

Collin, R. W. J. et al., *Mutations of ESRRB Encoding Estrogen-Related Receptor Beta Cause Autosomal-Recessive Nonsyndromic Hearing Impairment DFNB35*, The American Journal of Human Genetics, 82, (2008), pp. 125-138.

Collins, C. A. et al., *Stem Cell Function, Sef-Renewal, and Behavioral Heterogenity of Cells From the Adult Muscle Statellite Cell Niche*, Cell, vol. 122, (2005), pp. 289-301.

Conrad, S. et al., *Generation of Pluripotent Stem Cells From Adult Human Testis*, Nature, vol. 456, (2008), pp. 344-349, 1044.

Cowan, C. A. et al., *Derivation of Embryonic Stem-Cell Lines From Human Blastocysts*, The New England Journal of Medicine, 350, 13, (2004), 1353-1356.

Durcova-Hills, G., *Induced Reprogramming of Human Somatic Cells Into Pluripotency: a New Way How to Generate Pluripotent Stem Cells*, Differentiation 76, (2008), pp. 323-325.

Endo, T. et al., *Label-Free Cell-Based Assay Using Localized Surface Plasmon Resonance Biosensor*, Analytica Chimica Acta, 614, (2008), pp. 182-189.

Gill, D. S. et al., *Biopharmaceutical Drug Discovery Using Novel Protein Scaffolds*, Current Opinion Biotechnology, 17, (2006), pp. 653-658.

Hanna, J. et al., *Direct Reprogramming of Terminally Differentiated Mature B. Lymphocytes to Pluripotency*, Cell, 133, (2008), pp. 250-264.

Haustein, E. et al., *Fluorescence Correlation Spectroscopy: Novel Variations of an Established Technique*, Annu. Rev. Viophys. Biomol. Struct. 36, (2007), pp. 151-169.

Hentschke, M. et al., *Domains of ERRγ That Mediate Homodimerization and Interaction With Factors Stimulating DNA Binding*, Eur. J. Biochem., 269, (2002), pp. 4086-4097.

Holt, L. J. et al., *Domain Antibodies: Proteins for Therapy*, Trends in Biotechnology, vol. 21, No. 11, (2003), pp. 484-490.

Hyatt, S. M. et al., *On the Intractability of Estrogen-Related Receptor α as a Target for Activation by Small Molecules*, J. Med. Chem., 50, (2007), pp. 6722-6724.

Ijichi, N. et al., *Estrogen-Related Receptor α Modulates the Expression of Adipogenesis-Related Genes During Adipoycte Differentation*, Biochemical and Biophysical Research Communications, 358, (2007), pp. 813-818.

Iliades, P. et al., *Triabodies: Single Chain Fv Fragments Without a Linker Form Trivalent Trimers*, FEBS Letters, vol. 409, Issue 3, (1997), pp. 437-441.

Ivanova, N. et al., *Dissecting Self-Renewal in Stem Cells With RNA Interference*, Nature, vol. 442, (2006), pp. 533-538, 1-36.

Jaenisch, R. et al., *Stem Cells, the Molecular Circuitry of Pluripotency and Nuclear Reprogramming*, Cell, 132, (2008), pp. 567-582.

Jiang, J. et al., *A Core Klf Circuitry Regulates Self-Renewal of Embryonic Stem Cells*, Nature Cell Biology, vol. 10, No. 3, (2008), pp. 353-360, 1-16, 1-7.

Kallen, J. et al., *Crystal Structure of Human Estrogen-Related Receptor α in Complex With a Synthetic Inverse Agonist Reveals Its Novel Molecular Mechanism*, The Journal of Biological Chemistry, vol. 282, No. 32, (2007), pp. 23231-23239.

Kermani, A. J. et al., *Characterization and Genetic Manipulation of Human Umbilical Cord Vein Mesenchymal Stem Cells: Potential Application in Cell-Based Gene Therapy*, Rejuvenation Research, vol. 11, No. 2, (2008), pp. 379-386.

Kim, J. B. et al., *Pluripotent Stem Cells Induced from Adult Neural Stem Cells by Reprogramming With Two Factors*, Nature, vol. 454, (2008), pp. 646-650.

Kim, S. et al., *ERK-½ and p38 Kinase Oppositely Regulate Nitric Oxide-Induced Apoptosis of Chondrocytes in Association with p53, Caspase-3, and Differentiation Stauts*, The Journal of Biological Chemistry, vol. 277, No. 2, (2002), pp. 1332-1339.

Kristov, A. V. et al., *Transformation From Committed Progenitor to Leukaemia Stem Cell Intiated by MLL-AF9*, Nature, vol. 442, (2006), pp. 818-822.

Kwon, Y. et al., *Quantitative Evaluation of the Relative Cell Permability of Peptoids and Peptides*, J. Am. Chem. Soc., 129, (2007), pp. 1508-1509.

Lewitzky, M. et al., *Reprogramming Somatic Cells towards Pluripotency by Defined Factors*, Current Opinion in Biotechnology, 18, (2007), pp. 467-473.

Liang, J. et al., *Nanog and Oct4 Associate with Unique Transcriptional Repression Complexes in Embryonic Stem Cells*, Nature Cell Biology, 10, (2008), pp. 1-9, 1-7.

Lidke, D. S. et al., *In Vivo Imaging Using Quantum Dot—Conjugated Probes*, Current Protocols in Cell Biology, 36, (2007), pp. 25.1.1-25.1.18.

Liu, B. et al., *Characterization of TectoRNA Assembly With Cationic Conjugated Polymers*, J. Am. Chem. Soc., 126, (2004), pp. 4076-4077.

Liu, X. et al., *Receptor Binding Characteristics of the Endocrine Disruptor Bisphenol A for the Human Nuclear Estrogen-Related Receptor γ, Chief and Corroborative Hydrogen Bonds of the Bisphenol A Phenol-Hydroxyl Group with Arg316 and Glu275 Residues*, FEBS Journal, 274, (2007), pp. 6340-6351.

Loth, Y. et al., *The Oct4 and Nanog Transcription Network Regulates Pluripotency in Mouse Embryonic Stems Cells*, Nature Genetics, vol. 38, No. 4, (2006), pp. 431-440.

Lowry, W. E. et al., *Generation of Human Induced Pluripotent and Stem Cells From Dermal Fibroblasts*, PNAS, vol. 105, No. 8, (2008), 2883-2888.

Maherali, N. et al., *A High Efficiency System for the Generation and Study of Human Induced Pluripotent Stem Cells*, Cell Stem Cell, 3 (2008), pp. 340-345.

Maherali, N. et al., *Directly Reprogrammed Fibroblats Show Global Epigenetic Remodeling and Widespread Tissue Contribution*, Cell Stem Cell, 1, (2007), 55-70.

Masui, S. et al, *Pluripotency Governed by Sox2 Via Regulation of Oct³/₄ Expression in Mouse Embryonic Stem Cells*, Nature Cell Biology, vol. 9, No. 6, (2007), pp. 625-635, 1-4.

Matoba, R. et al., *Dissection Oct³/₄-Regulated Gene Networks in Embryonic Stem Cells by Expression Profiling, Pou5f1-Regulated Genes*, PLoS ONE, Issue 1, (2006), 1-15.

Matsushima, A. et. al., *ERRγ Tethers Strongly Bisphenol A and 4-α-cumylphenol in an Induced-Fit Manners*, Biochemical and Biophysical Research communications, 373 (2008), pp. 408-413.

Meissner, A. et al., *Direct Reprogramming of Genetically Unmodified Fibroblasts into Pluripotent Stems Cells*, Nature Biotechnology, vol. 25, No. 10, (2007), pp. 1177-1181.

Mikkelsen, T. S. et al., *Dissecting Direct Reprogramming Through Integrative Genomic Analysis*, Nature, vol. 454, (2008), p. 794.

Mosavi, L. K. et al., *The Ankyrin Repeat as Molecular Architecture for Protein Recognition*, Protein Science, 13, (2004), pp. 1435-1448.

Mullen, E. M. et al., *Nuclear Receptors in Regulation of Mouse ES Cell Pluripotency and Differentiation*, PPAR Resarch, Article ID 61563, vol. 2007, 10 pages.

Okita, K. et al., *Generation of mouse Induced Pluripotent Stem Cells Without Viral Vectors*, Science, vol. 32, (2008), pp. 949-953.

Okita, K. et al., *Generation of Germline-Competent Induced Pluripotent Stem Cells*, Nature, vol. 448, (2007), pp. 313-317.

Orsetti, B. et al., *Genetic Profiling of Chromosome I in Breast Cancer: Mapping of Regions of Gains and Losses and Identification of Candidate Genes on I q*, British Journal of Cancer, 95, (2006), pp. 1439-1447.

Park, I. et al., *Disease Specific Induced Pluripotent Stem Cells*, Cell, 134, (2008), pp. 877-886.

Park, I. et al., *Reprogramming of Human Somatic Cells to Pluripotency with Defined Factors*, Nature, vol. 451, (2007), pp. 141-146.

Park, Y. et al., *An Autoregulatory Loop Controlling Orphan Nuclear Receptor DAX-1 Gene Expression by Orphan Nuclear Receptor ERRγ*, Nucleic Acids Research, vol. 33, No. 21, (2005), pp. 6756-6768.

Rando, T. A., *The Adult Muscle Stem Cell Comes of Age*, Nature Medicine, vol. 11, No. 8, (2005), pp. 829-831.

(56) References Cited

OTHER PUBLICATIONS

Sanyal, S. et al., *Deoxyriboneucleic Acid Response Element-Dependent Regulation of Transcription by Orphan Nuclear Receptor Estrogen Receptor-Related Receptor γ*, Molecular Endocrinology, 18(2), (2004), pp. 312-325.

Schuldiner M. et al., *Induced Neuronal Differentiation of Human Embryonic Stem Cells*, Brain Research, 913, (2001), pp. 201-205.

Silverman, J. et al., *Multivalent Avimer Proteins Evolved by Exon Shuffling of a Family of Human Receptor Domains*, Nature biotechnology, vol. 23, No. 12, (2005), pp. 1556-1561.

Skerra A., *Engineered Protein Scaffolds for Molecular Recognition*, Journal of Molecular Recognition, 13, (2000), pp. 167-187.

Stadtfeld, M. et al., *Reprogramming of Pancreatic β Cells into Induced Pluripotent Stem Cells*, Current Biology, 18, (2008), pp. 890-894.

Stadtfeld, M. et al., *Induced Pluripotent Stem Cells Generated Without Viral Intergration*, Science, vol. 322, (2008), pp. 945-949.

Stone, E. et al., *The Assembly of Single Domain Antibodies into Bispecific Decavalent Molecules*, Journal of Immunological Methods, 318, (2007), pp. 88-94.

Suetsugi, M. et al., *Flavone and Isoflavone Phytoestrogens are Agonists of Estrogen-Related Receptors*, Molecular Cancer Research, vol. 1, (2003), pp. 981-991.

Sun, P. et al., *Expression of Estrogen Receptor-Related Receptors, a Subfamily of Orphan Nuclear Receptors, as New Tumor biomarkers in Ovarian Cancer Cells*, J. Mol. Med., 83, (2005), pp. 457-467.

Szabó, P. E., *Allele-Specific Expression of Imprinted Genes in Mouse Migratory Primordial Germ Cells*, Mechanisms of Development, 115, (2002), pp. 157-160.

Takahashi, K. et al., *Induction of Pluripotent Stem From Mouse Embryonic and adult Fibroblast Cultures by Defined Factors*, Cell, 126, (2006), pp. 663-676.

Takahashi, K. et al., *Induction of Pluripotent Stem Cells From Adult Human Fibroblasts by Defined Factors*, Cell, 131, (2007), pp. 861-872.

Thompson, N. L. et al., *Recent Advances in Fluroescence Correlation Spectroscopy*, Current Opinion in Structural Biology, 12, (2002), pp. 634-641.

Thomson, J. A. et al., *Embryonic Stem Cell Derived from Human Blastocysts*, Science, vol. 282, (1998), pp. 1145-1147.

Tremblay, A. M. et al.., *Phosphorylation-Dependent Sumoylation Regulates Estrogen-Related Receptor-α, and -γ Transcriptional Activity Through a Synergy Control Motif*, Molecular Endocrinology, 22(3), (2008), pp. 570-584.

Wang, J. et al., *A Protein Interaction Network for Pluripotency of Embryonic Stem Cells*, Nature, vol. 444, (2006), pp. 364-368, 1-11, and 11 pages.

Welstead, G. G. et al., *The Reprogramming Language Pluripotency*, Current Opinion in Genetics & Developmnet, 18, (2008), pp. 1-7.

Wernig, M. et al., *In Vitro Reprogramming of Fibroblasts into a Pluripotent ES-cell like State*, Nature, vol. 448, pp. 318-324.

Xie, W. et al., *Constitutive Activation of Transcription and Binding of Coactivator by Estrogen-Related Receptors 1 and 2*, Molecular Endocrinology, vol. 13, No. 12, (1999), pp. 2151-2162.

Xie, X. S. et al., *Single-Molecule Approach to Molecular Biology in Living Bacterial Cells*, Annu. Rev. Biophys., 37, (208), p. 417-444.

Yu, D. D. et al., *Indentification of an Agonist Ligand for Estrogen-Related Receptors ERRβ/γ*, Bioorganic & Medicinal Chemistry Letters, 15, (2005), pp. 1311-1313.

Yu, J. et al., *Induced Pluripotent Stem Cell Lines Derived from Human Somatic Cells*, Science, vol. 38, (2007), pp. 1917-1920, 2-23.

Zhou, Q. et al., *A Gene Regulatory network in Mouse Embryonic Stem Cells*, PNAS, vol. 104, No. 42, pp. 16438-16443.

Zuercher, W. J. et al., *Identification and Structure—Activity Relationship of Phenolic Acyl Hydrazones as Selective Agonists for the Estrogen-Related Orphan Nuclear Receptors EERβ and ERRγ*, J, Med. Chem., 48, (2005), pp. 3107-3109.

Feng, B. et al., *Reprogramming of Fibroblasts into Induced Pluripotent Stem Cells With Orphan Nuclear Receptor Esrrb*, Nature Cell Biology, vol. 11, No. 2, Feb. 2009, 197-203, 1-13.

Heng, J.-C.D. et al., *Transcription Factors for the Modulation of Pluripotency and Reprogramming*, Cold Spring Harbor Symposia Quantitative Biology, vol. 75, (2010) 237-244.

Martinez-Jimenez, C. P. et al., *Underexpressed Coactivators PGC1α and SRC1 Impair Hepatocyte Nuclear Factors 4α Function and Promote Dedifferentiation in Human Hepatoma Cells*, Journal of Biological Chemistry, vol. 281, No. 4, Oct. 6, 2006, 29840-29849, 1-7.

Supplementary Search Report for European Application No. 08 87 4225 dated Oct. 12, 2012.

Supplementary European Search Report from corresponding European Patent Application No. 08 87 4225, dated Oct. 11, 2012.

Extended European Search Report from corresponding European Patent Application No. 08 87 4225, dated Oct. 22, 2012.

International Search Report from corresponding International Patent Application No. PCT/SG2008/000407, mailed Dec. 18, 2008.

Written Opinion from corresponding International Patent Application No. PCT/SG2008/000407, mailed Dec. 18, 2008.

International Preliminary Report on Patentability from corresponding International Patent Application No. PCT/SG2008/000407, date completed Aug. 5, 2010.

Office Action from corresponding Japanese Patent Application No. 2011-508447, forwarding date Oct. 1, 2013.

Yamanaka, Shinya; "Review: Prospects and Issues of Cardiovascular Therapy with ES Cells"; *Blood Vessel*; 2005, vol. 28, No. 2; pp. 33-38, Abstract Only.

Yamanaka, Shinya, "Long-Term Self-Renewal Capacity and Tumorigenicity of ES Cells"; *The Medical Frontier*; Aug. 2005, vol. 60, No. 8, pp. 1677-1682, Abstract Only.

Zhou, Wei, et al.; "Indentification and Characterization of Two Novel Splicing Isoforms of Human Estrogen-Related Receptor β"; *The Journal of Endocrinology & Metabolism*; 91(2):569-579.

* cited by examiner

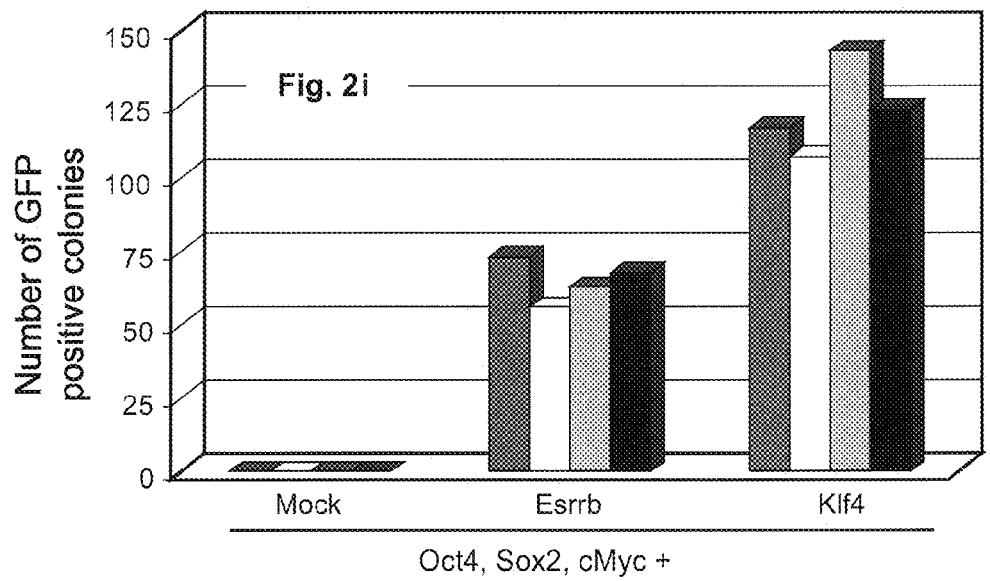
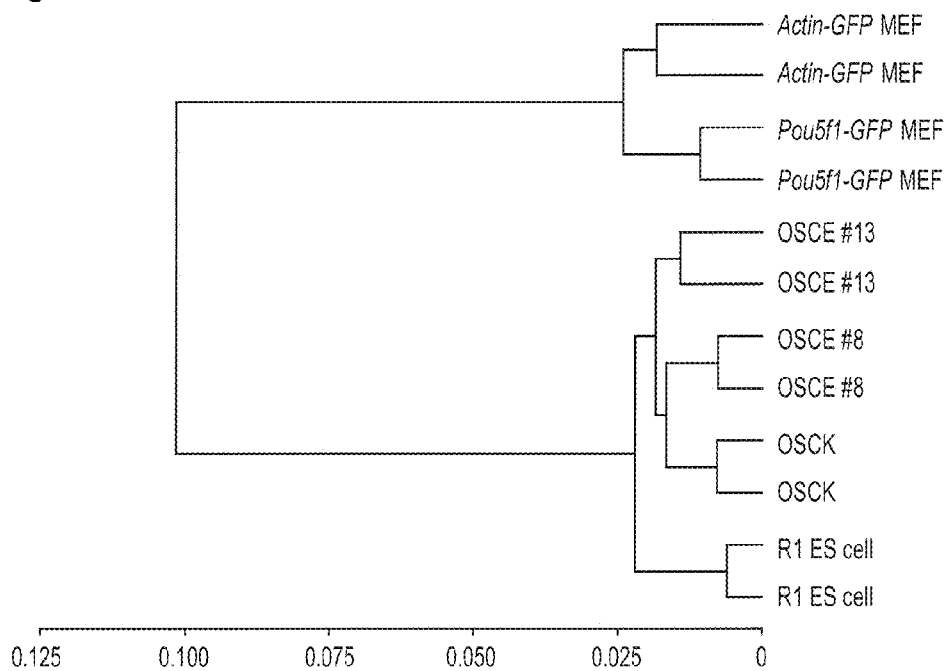
Fig. 3a

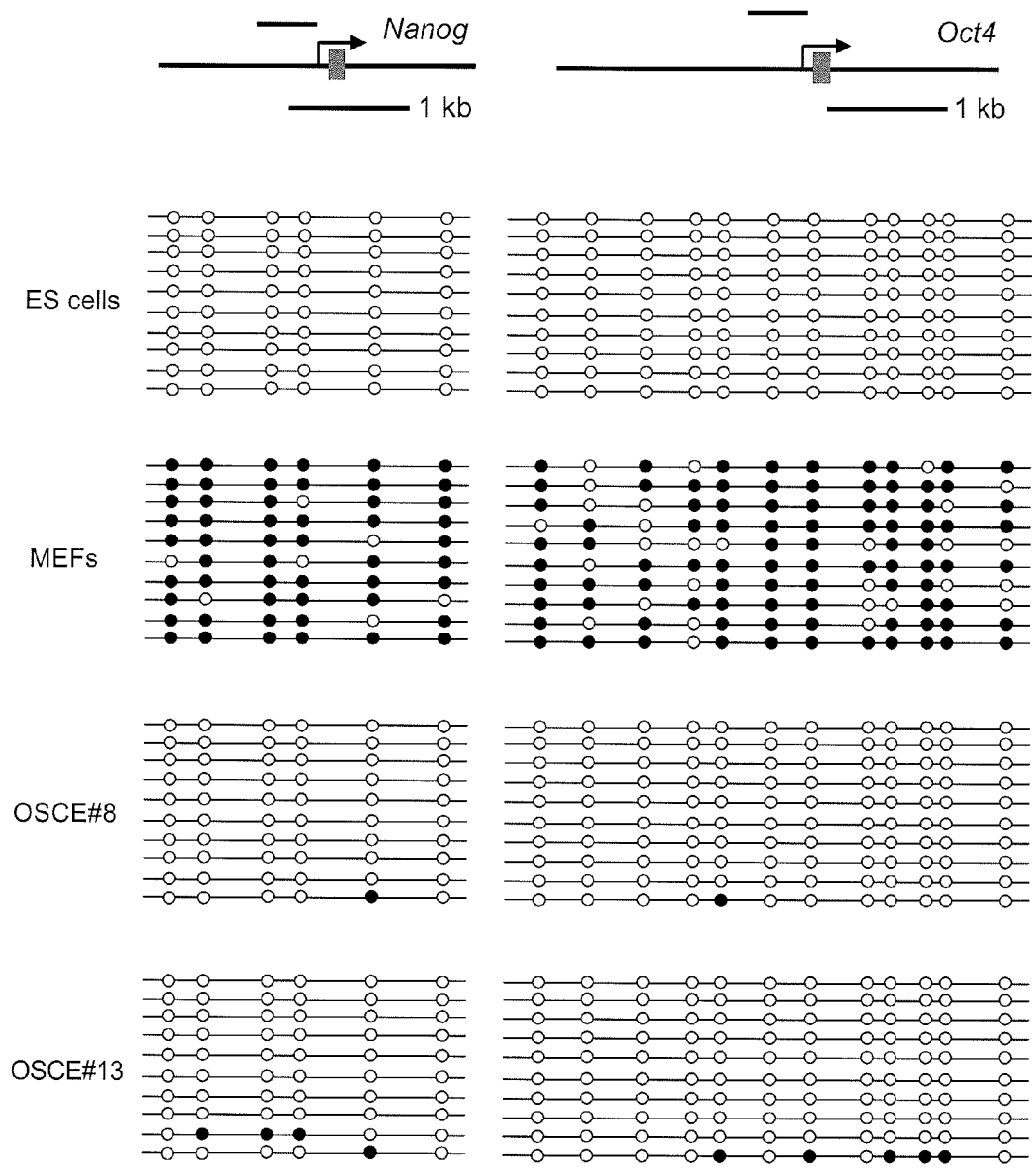

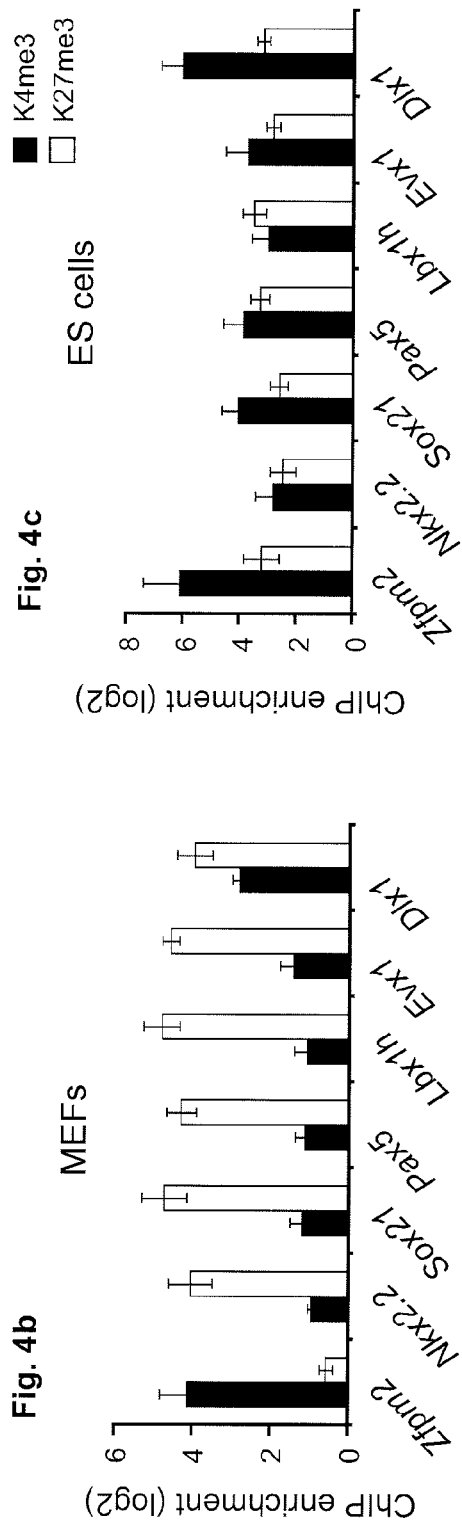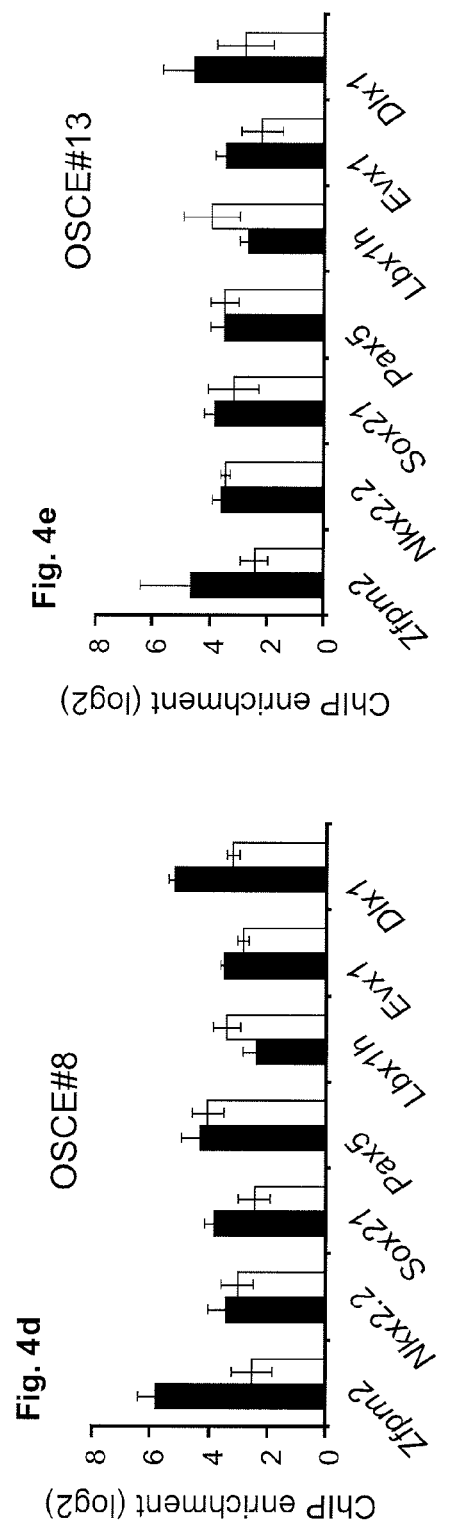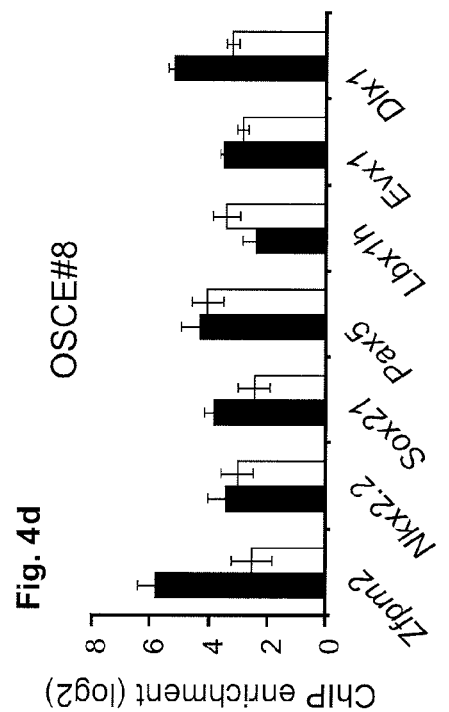

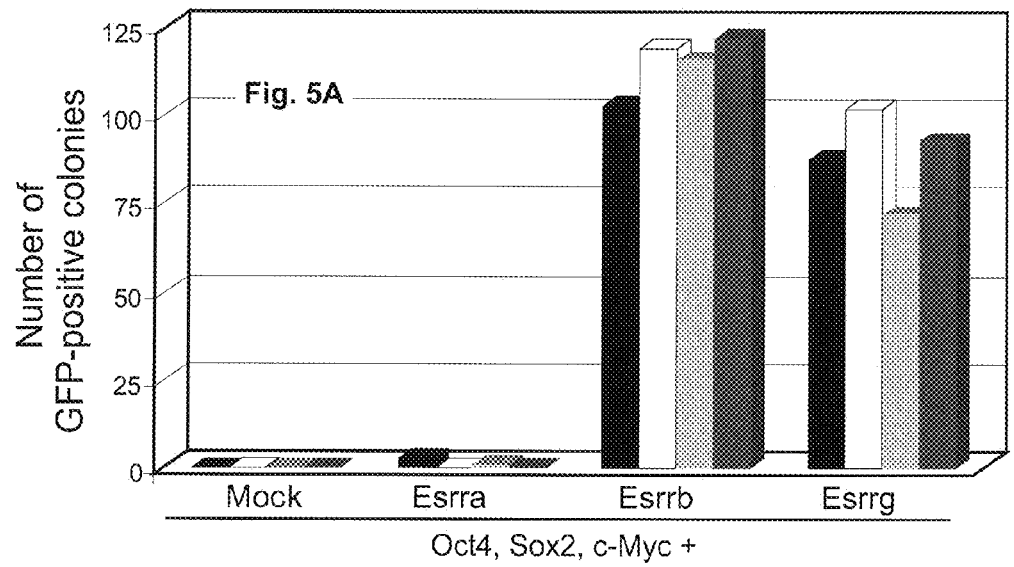
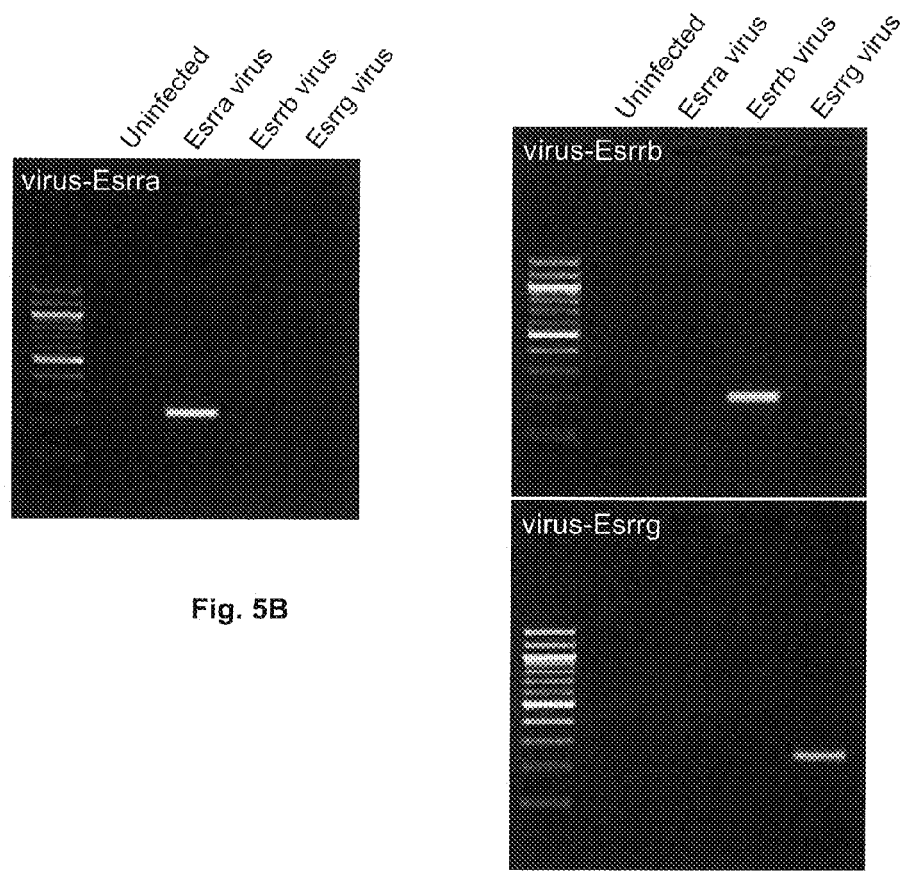
Fig. 5B

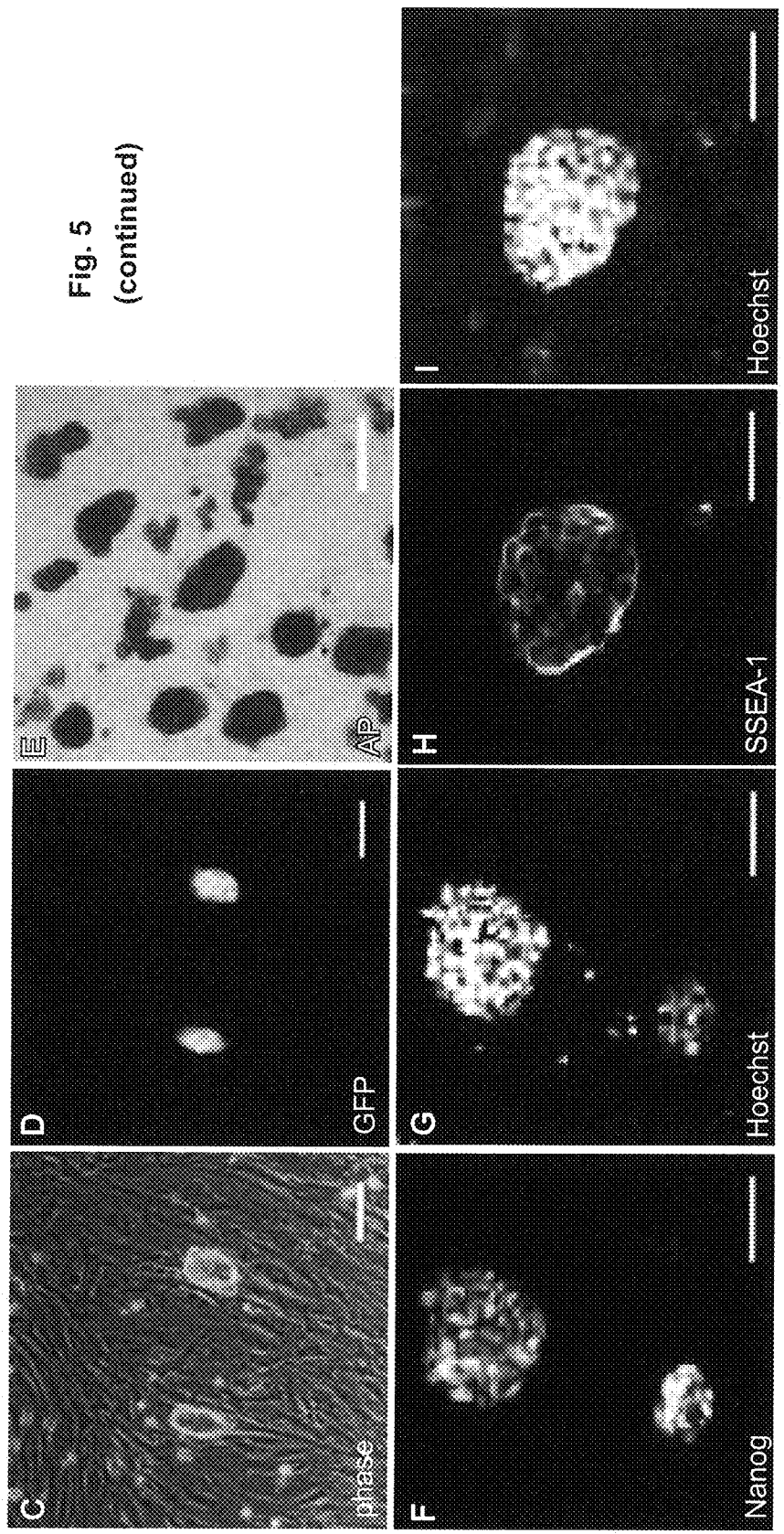

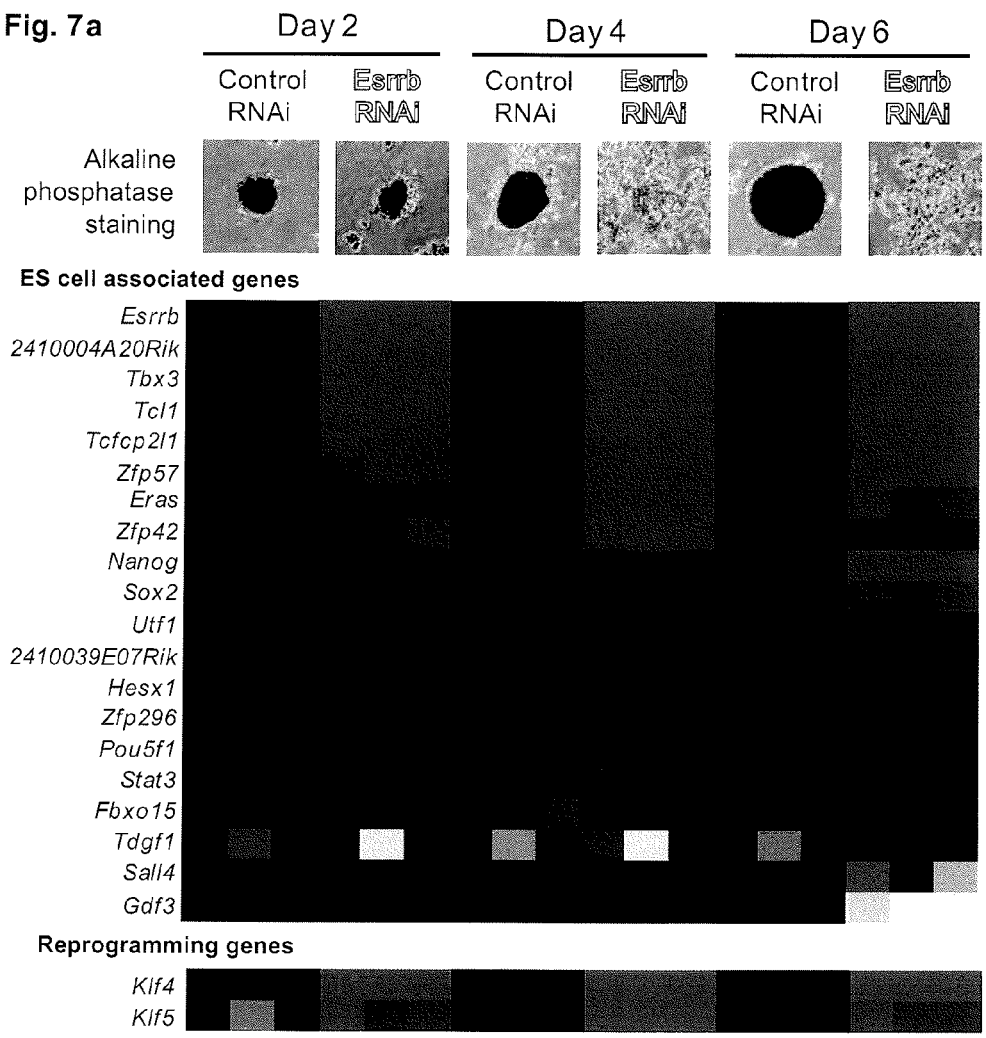
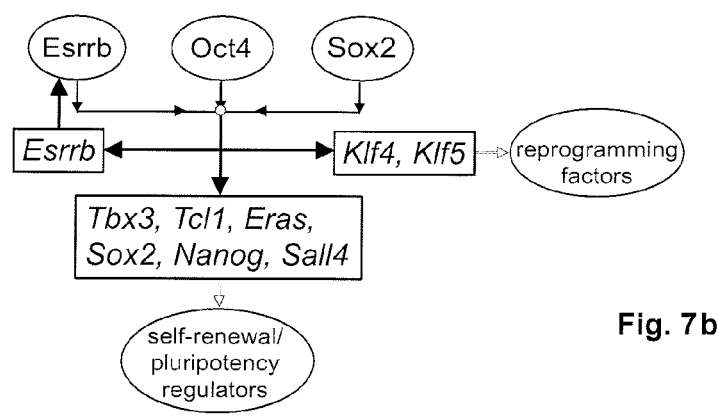
Fig. 7b

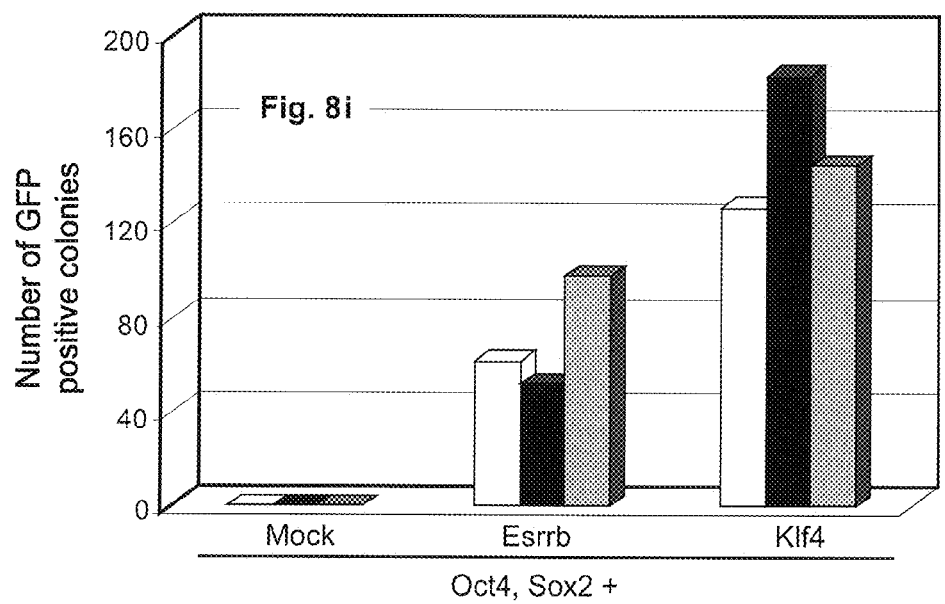
Fig. 8i
Fig. 9a
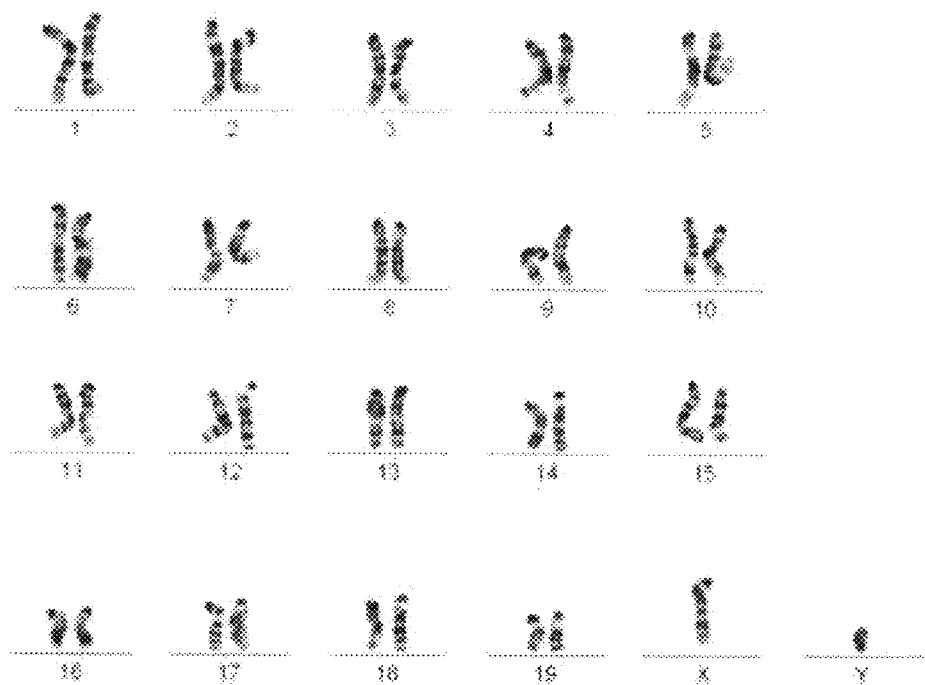

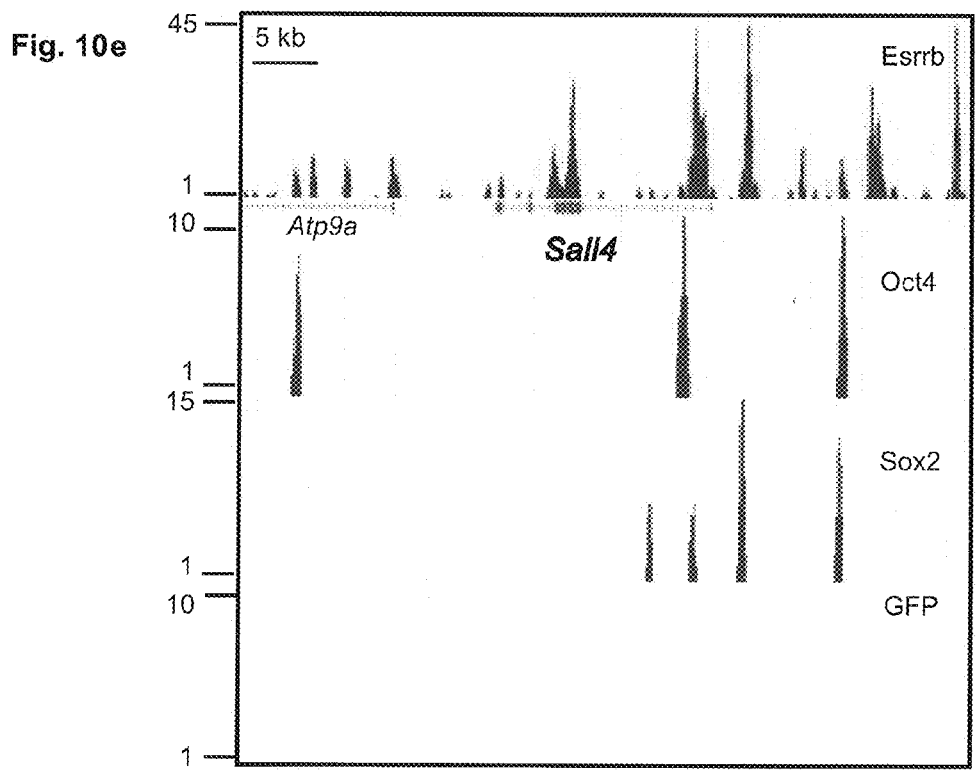
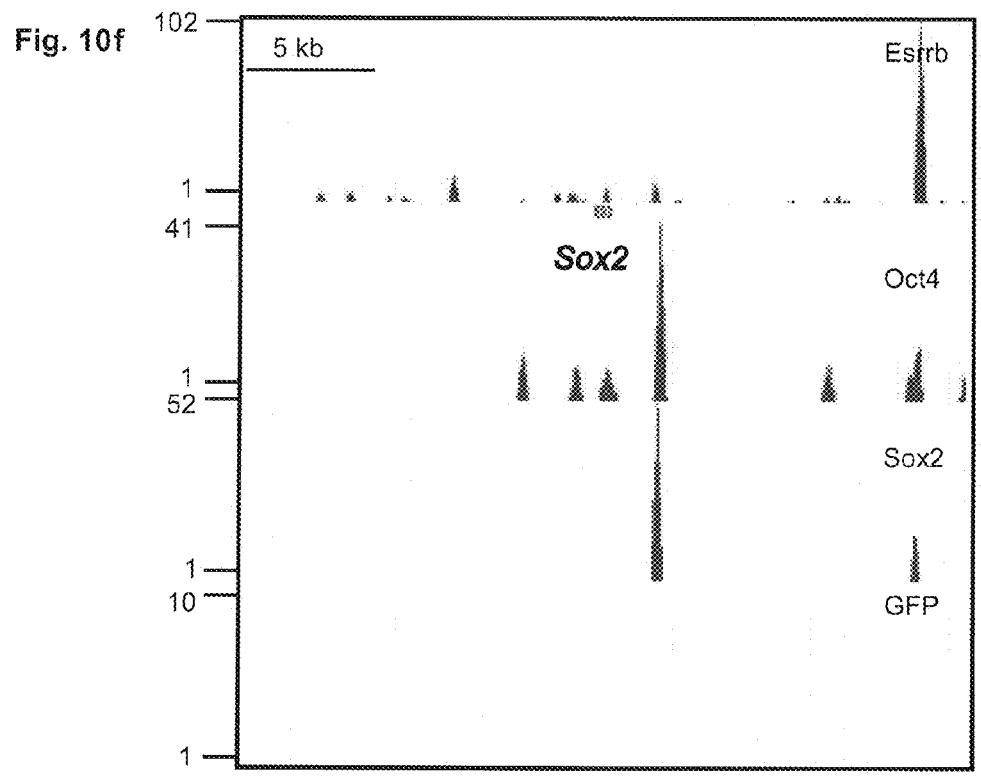

METHOD OF EFFECTING DE-DIFFERENTIATION OF A CELL

CROSS-REFERENCE TO RELATED APPLICATIONS

This application is a national stage application filed under 35 U.S.C. 371 of International Application No. PCT/SG2008/000407, filed Oct. 21, 2008, which makes reference to and claims the benefit of priority of an application for "Methods For Modulating The Differentiation Status Of A Cell" filed on May 6, 2008 with the United States Patent and Trademark Office and there duly assigned the Ser. No. 61/050,726. The contents of said application filed on May 6, 2008 is incorporated herein by reference for all purposes, including an incorporation of any element or part of the description, claims or drawings not contained herein and referred to in Rule 20.5(a) of the PCT, pursuant to Rule 4.18 of the PCT.

FIELD OF THE INVENTION

The present invention relates to a method of effecting de-differentiation of a cell into a less differentiated cell, including into a pluripotent cell. The method thus allows inter alia forming induced pluripotent stem cells from differentiated somatic cells. The method also allows maintaining pluripotency of an undifferentiated cell.

BACKGROUND OF THE INVENTION

Transcription factors can exert a dominant effect in specifying gene expression program and impart unique cellular property. Important regulators of pluripotency, Oct4, Sox2 and Nanog, are transcription factors. Of these three proteins, Oct4 and Nanog have roles that are specific to pluripotent cells. Pluripotency is the ability of a cell to give rise to a cell of any desired tissue of an organism. Further transcription factors such as Stat3, P53 and others are thought to play a role in a regulatory network that controls pluripotency.

The multitude of cells such as cells of the human or animal body is generated through the process of differentiation. It was previously surmised that as stem cells differentiate, they lose their ability to make cell fate decision and become more restricted in their potential. However, the developmentally restricted state of differentiated somatic cells can also be reversed to a pluripotent state through several strategies of reprogramming (for an introduction see Jaenisch, R., & Young, R., Cell (2008) 132, 567-582; cf. also FIG. 1). Among these methods are somatic cell nuclear transfer using enucleated unfertilized oocyte, fusion of differentiated cells with pluripotent cells and treatment of differentiated cells using extracts derived from pluripotent cells (Lewitzky, M. & Yamanaka, S., Curr. Opin. Biotechnol. (2007) 18, 467-473). The somatic cell nuclear transfer has in the meantime also been applied to a fertilized embryo as a recipient (WO 2008103462).

Reprogramming of somatic cells to pluripotent cells can also be achieved by the retrovirus mediated transduction of defined transcription factors. Conversion of murine and human fibroblasts to pluripotent cells known as induced pluripotent stem (iPS) cells can be achieved using the four transcription factors Oct4, Sox2, c-Myc and Klf4 (see e.g. Takahashi, K. & Yamanaka, S., Cell (2006) 126, 663-676; Lowry, W. E., et al., Proc. Natl. Acad. Sci. (2008) 105, 8, 2883-2888). The obtained iPS cells are developmentally and epigenetically indistinguishable from embryonic stem (ES) cells (ibid.) and have expression profiles that are highly similar to wild-type embryonic stem cells (Mikkelsen, T. S., et al., Nature (2008) 454, 49-55, corrigendum in Nature (2008) 454, 794-794). By overexpressing these transcription factors, differentiated fibroblasts from human ES cells, primary fetal tissues, neonatal skin fibroblasts, adult fibroblasts and adult mesenchymal stem cells can be reprogrammed to iPS cells (Park, I-H, et al., Nature (2007) 451, 141-147). Successful reprogramming of fibroblasts to iPS cells requires the heterologous expression of these four transcription factors for at least 14 days (Brambrink, T., et al., Cell Stem Cell (2008) 2, 151-159).

Mature, fully differentiated B lymphocytes, pancreatic β cells, hepatocytes, keratinocytes and gastric epithelial cells can also be reprogrammed into iPS cells by expressing heterologous Oct4, Sox2, c-Myc and Klf4 using inducible lentiviral vectors or pMXs-based retroviruses (Takahashi, K., et al., Cell (2007) 131, 861-872; Hanna, J.; et al., Cell (2008) 133, 250-264; Stadtfeld, M., et al., Current Biology (2008) 18, 12, 890-894; Maherali, N., et al., Cell Stem Cell (2008) 3, 340-345; for an overview see e.g. Welstead, G. G., et al., Current Opinion in Genetics & Development (2008) 18, doi: 10.1016/j.gde.2008.01.013, or Durcova-Hills, G., et al., Differentiation (2008) 76, 323-325; Aoi, T., et al., Science (2008) 321, 699-702). Mesenchymal cells and myeloid cells from human ES cells, as well as primary fibroblasts and newborn foreskin fibroblasts can also be reprogrammed into iPS cells by expressing heterologous Oct4, Sox2, Nanog and Lin28 using a lentiviral vector (Yu, J., et al., Science (2007) 318, 191-920). After the priority date of the present application even adult neural stem cells have been reprogrammed to induced pluripotent stem cells with heterologous Oct4 and either Klf4 or c-Myc (Kim, J. B., et al., Nature (2008) 454, 646-650).

The ability of embryonic stem cells to readily differentiate furthermore continues to pose a major practical challenge. In order to maintain embryonic stem cells in a pluripotent state, their differentiating during handling and growing in culture has to be prevented. For this reason they are traditionally cultured in the presence of fetal calf serum on a layer of feeder cells (see e.g. U.S. Pat. No. 5,843,780 and U.S. Pat. No. 6,090,622) or in fibroblast-conditioned medium (CM). Nevertheless, even under carefully controlled conditions embryonic stem cells may undergo spontaneous differentiation during in-vitro propagation. Leukaemia inhibitory factor, a factor mediating self-renewal in mouse embryonic stem cells, has also been found to inhibit differentiation of mouse embryonic stem cells, but it does not replace the role of feeder cells in preventing differentiation of human embryonic stem cells. Therefore, means of maintaining pluripotency and/or self-renewing characteristics of embryonic stem cells would be a substantial achievement towards realizing the full commercial potential of stem cell therapy.

It is an object of the present invention to offer an alternative method of reprogramming somatic cells and of maintaining pluripotency of an undifferentiated cell.

This object is solved by increasing the amount or the activity of an Err protein, or a functional fragment thereof.

SUMMARY OF THE INVENTION

In a first aspect the present invention provides a method of effecting de-differentiation of an at least partially differentiated cell or of maintaining pluripotency and/or self-renewing characteristics of an undifferentiated cell. The method includes increasing the amount or the activity of an Err protein, or a functional fragment thereof, in the cell.

In a second aspect the invention relates to a dedifferentiated cell obtained by the method of the first aspect.

In a third aspect the invention provides a method of identifying a candidate compound capable of effecting de-differentiation of an at least partially differentiated cell or a method of maintaining pluripotency and/or self-renewing characteristics of an undifferentiated cell. The method includes introducing the compound into a cell that is capable of expressing an Err protein, or a functional fragment thereof. The method further includes determining the expression of the Err protein. An increased expression of the Err protein is an indication that the compound is capable of effecting de-differentiation of an at least partially differentiated cell or of maintaining pluripotency and/or self-renewing characteristics of an undifferentiated cell.

In a fourth aspect the invention provides an in-vitro method of identifying a compound that is capable of effecting de-differentiation of an at least partially differentiated cell or of maintaining pluripotency and/or self-renewing characteristics of an undifferentiated cell. The method includes contacting the compound, an Err protein, or a functional fragment thereof, and at least one of Nanog and Oct4. The facilitation of the formation of a complex between the Err protein and at least one of Nanog and Oct4 indicates that the compound is capable of effecting de-differentiation of an at least partially differentiated cell or of maintaining pluripotency and/or self-renewing characteristics of an undifferentiated cell.

In a fifth aspect the invention relates to the use of a nucleic acid molecule and/or a compound that increases the absolute quantity of an Err protein in a cell, in the manufacture of an agent for effecting de-differentiation of an at least partially differentiated cell or for maintaining pluripotency and/or self-renewing characteristics of an undifferentiated cell.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention will be better understood with reference to the detailed description when considered in conjunction with non-limiting examples below and the accompanying drawings.

In FIG. 2i the efficiency of Esrrb in mediating reprogramming is compared to Klf4 using Pou5fl-GFP MEF. Shown are the numbers of GFP positive colonies induced by Esrrb or Klf4 in conjunction with Oct4, Sox2 and cMyc at 14 dpi. iPS: induced pluripotent stem cells; dpi: days post infection; Bars: 200 μm (FIG. 2a, FIG. 2b, FIG. 2g, FIG. 2h); 100 μm (FIGS. 2c-f).

FIG. 4 depicts an analysis of epigenetic states of Esrrb reprogrammed cells. Promoter methylation analysis of reprogrammed cells is shown in FIG. 4a. The methylation status of the Nanog and Oct4 promoters was analyzed using bisulfite sequencing. Open circles indicate unmethylated and filled circles indicate methylated CpG dinucleotides. Shown are ten representative clones sequenced from ES cells (V6.4), MEFs (CD 1), Esrrb reprogrammed cells (OSCE#8 and OSCE#13 clones). FIGS. 4b-e shows the results of real-time PCR after chromatin immunoprecipitation (ChIP) using antibodies against tri-methylated histone H3K4 and H3K27 with an extract obtained from ES cells (V6.4), MEFs (CD1), and Esrrb reprogrammed cells (OSCE#8 and OSCE#13 clones). Shown are the log 2 enrichments for several previously reported 'bivalent' loci in ES cells. Data are presented as the mean+/−s.e.m. and derived from three independent experiments (n=3).

FIGS. 6a-c show the bright field images for 3 embryos; FIGS. 6d-f show the extensive incorporation of EGFP positive cells in the chimeric embryos. FIGS. 6g-i show the distribution of EGFP-positive cells in parasagittal sections of chimeric embryos. EGFP-positive cells are widely and extensively distributed among all tissues and organs and are represented in tissues derived from all three major germ layers (ectoderm, mesoderm and endoderm) of the developing embryo. Abbreviations: F, forebrain; Fg, foregut diverticum; H, heart, Hb, hindbrain; M, midbrain; Ne, neuroepithelium; O, otic vesicle; S, somite.

FIG. 7 illustrates that Esrrb regulates genes encoding for factors involved in self-renewal, pluripotency, reprogramming and epigenetic modification. Time course microarray analyses were performed to measure gene expression changes at different days after Esrrb knockdown (FIG. 7a). The morphology and alkaline phosphatase (AP) staining are shown for each time point for both the control and Esrrb depleted cells. Note that the colony morphology and alkaline phosphatase expression was maintained at day 2, indicating that the ES cells remained undifferentiated. Shown are Microarray heatmaps depicting expression changes of selected ES cell-associated and reprogramming genes at different days, suggesting the regulation of Esrrb on these genes. Red indicates increased expression compared to control samples, whereas green means decreased expression. The genes expression levels were mean centered to show their relative change. FIG. 7b depicts a model on the role of Esrrb in ES cells. Esrrb auto-regulates its expression through feedback loop. Esrrb, Oct4 and Sox2 regulate genes involved in maintenance of pluripotency and self-renewal. These three transcription factors also positively regulate genes involved in reprogramming.

FIGS. 8d and 8f show the counterstaining with Hoechst. In the Pou5fl-GFP MEF, Esrrb, Oct4 and Sox2 triggered the GFP expression specifically in iPS colonies, but not in the surrounding fibroblastic cells, indicating the restoration of endogenous Oct4 (FIG. 8g & FIG. 8h). In FIG. 8i the efficiency of Esrrb in mediating reprogramming is compared to Klf4 using Pou5fl-GFP MEF. Shown are the numbers of GFP positive colonies induced by Esrrb or Klf4 in conjunction with Oct4 and Sox2 at 23 dpi. iPS: induced pluripotent stem cells; dpi: days post infection; Bars: 200 μm (FIGS. 8a,b,g,h); 100 μm (FIGS. 8c-f).

DETAILED DESCRIPTION OF THE INVENTION

Figure 1:
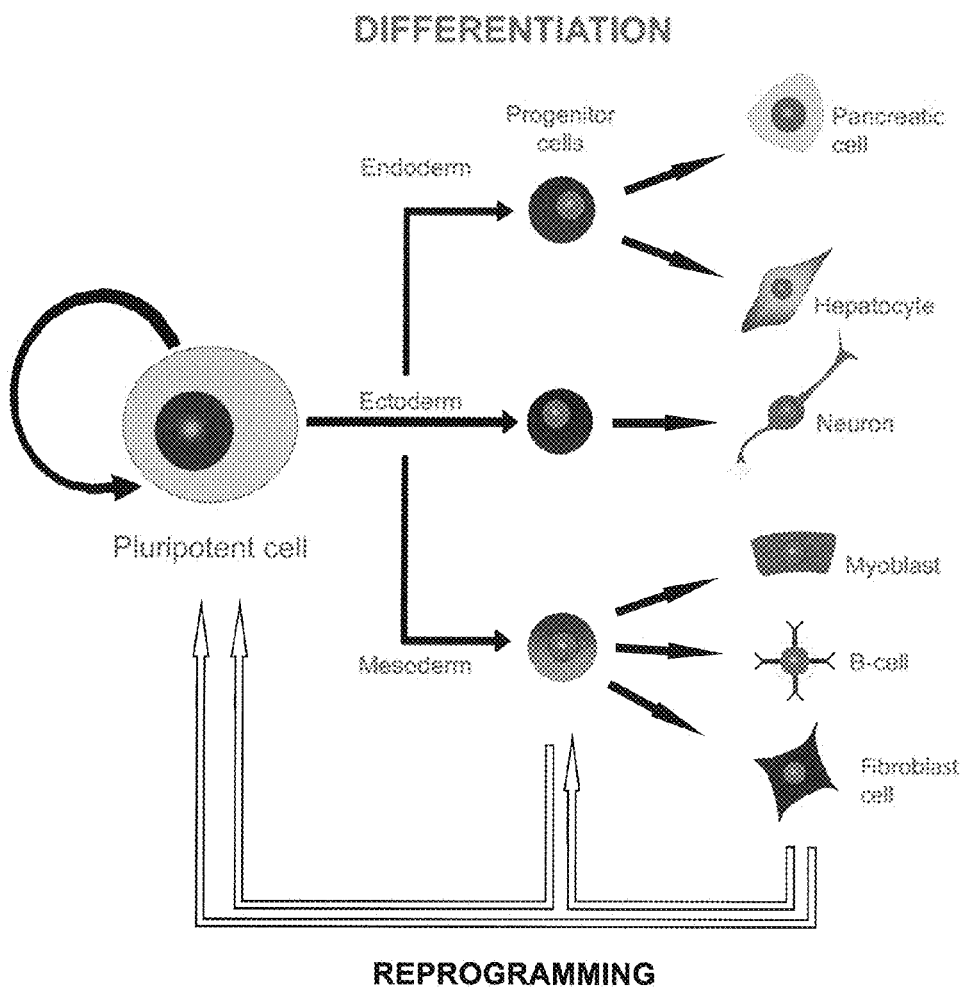
FIG. 1 outlines the processes of cell differentiation and of reprogramming a cell, i.e. inducing dedifferentiation. Stem cells are pluripotent and retain the capacity to differentiate into the mesoderm, ectoderm and endoderm lineages. Reprogramming, the reversion of cell fate commitment back to a less differentiated, including a pluripotent state, can be induced by the method of the present invention. Using the method of the invention, a pluripotent cell can also be arrested in its state (left).

The methods of the invention are based on modulating the amount of an estrogen related receptor (Err) protein, including modulating its expression, in a cell, such as a somatic cell, a progenitor cell or a stem cell. Illustrative examples of a suitable Err protein include, but are not limited to, Esrrb, Esrrd and Esrrg. Err proteins are a family of nuclear receptors acting as ligand-regulated transcription factors, which activates transcription in the absence of ligand. They have a high sequence similarity in the DNA binding domain with estrogen receptors, with which they share identical target response elements and coregulatory proteins. However, Err proteins do not respond to the classical ER ligand 17β-estradiol. Synthetic estrogenic compounds such as diethylstilbestrol and 4-hydroxytamoxifen (OHT) act as inverse agonists for the Err family members by disrupting Err-coactivator interactions. Transcriptional activation of hypoxic genes by hypoxia-inducible factor (HIF) has been found to be enhanced by Err proteins, and HIF and Err proteins have been shown to form complexes (Ao, A., et al., *Proc. Natl. Acad. Sci. U.S.A.* (2008) 105, 22, 7812-7826).

The estrogen-related receptor alpha (Esrra) protein, also termed ESRL1, Err1, Nr3b1, Estrra and ERRα, is regarded as a key regulator of mitochondrial biogenesis. It has also been implicated as a critical regulator of oxidative metabolism in muscle and termed a potential target for the activation in the treatment of metabolic disease (Hyatt, S. M., et al., *J. Med. Chem*. (2007) 50, 26, 6722-6724).

The estrogen related receptor β (Esrrb) protein, also termed Estrrb, ERRB, ERRβ, ERR2, ERRβ, ESRL2 and NR3B2 has been suggested as essential for proper hearing (Collin, R. W. J., et al., *The American Journal of Human Genetics* (2008) 82, 125-138). Esrrb has further been suggested as a marker for embryonic stem cells (Zhou, Q., et al., *Proc Natl. Acad. Sci. U.S.A.* (2007) 104, 42, 16438-16443). A screening has identified inter alia Essrb as an important gene regulator in embryonic stem cells, and it has further been suggested to be a coactivator acting together with, and being a direct target of, Oct4, Sox2, and Nanog (Zhou, Q., et al., *Proc Natl. Acad. Sci. U.S.A.* (2007) 104, 42, 16438-16443). Mass spectrometric analysis and affinity purification have identified the formation of a complex between Esrrb and Nanog (Liang, J., et al., *Nature Cell Biology* (2008) 10, 731-739; Wang, J., et al, *Nature* (2006) 444, 364-368). However, in human umbilical cord vein mesenchymal stem cells both Oct-4 and Nanog have been found to be expressed, but not Essrb (Kermani, A. J., et al., *Rejuvenation Res* (2008) 11, 2, 379-385). This finding has cast doubt on both the utility of Essrb as a universal stem cell marker and on the general importance of Essrb as a gene regulator. Based on the hypothesis that heterogenous cell populations exist in undifferentiated embryonic stem cells Carter et al. (*Gene Expression Patterns* (2008) 8, 181-198) have examined expression patterns of transcription factors in cultures of embryonic stem cells. They have found esrrb to be heterogeneously expressed ("mosaic-in-colony"), thereby again casting doubt on a universal role of esrrb in the gene regulation of stem cells.

Different isoforms of the estrogen related receptor γ (Esrrg) protein, also termed ERR3, Errγ, NR3B3, FLJ16023, KIAA0832 and DKFZp781L1617, that differ in the length of their N-terminal domains, have for example been found in mouse and human, where they have been termed isoforms 1 and 2. Esrrg has been found to be a specific receptor for the carcinogenic and hormonally active agent bisphenol A as well as 4-α-cumylphenol (Matsushima, A., et al., *Biochemical and Biophysical Research Communications* (2008) 373, 408-413). Similar to bisphenol A, 4-chloro-3-methyl phenol has been shown to associate and stabilize the ligand-binding domain of Esrrg (Abad, M. C., et al., *Journal of Steroid Biochemistry & Molecular Biology* (2008) 108, 44-54), competing for the inverse agonist 4-hydroxytamoxifen. Hence, bisphenol A can be regarded as an inverse antagonist of Esrrg, since it reverses deactivation by 4-hydroxytamoxifen to the originally high basal activation state in a dose-dependent manner (Liu, X., et al., *FEBS* (2007) 274, 6340-6351).

While Esrra has been found to be highly expressed in ovarian cancer cell lines and cancers, Esrrb could only be detected in a single cell line and in a single cancer analyzed (Sun, P., et al., *J. Mol. Med.* (2005) 83, 457-467). It is therefore currently unclear whether Esrrb could play a role in the development of cancer. Esrrg has previously been taken into consideration in a genetic profiling, but not been found to be of particular relevance in association with breast cancer (Orsetti, B., et al., *British Journal of Cancer* (2006) 95, 1439-1447).

The present invention is based on the surprising finding that the orphan nuclear receptors of the Err family work in conjunction with Oct4, Sox2 and c-Myc to mediate reprogramming of somatic cells, such as mouse embryonic fibroblasts, to iPS cells. Err reprogrammed cells share similar expression and epigenetic signatures of embryonic stem cells. An exemplary comparison with 14 further factors (transcription factors and chromatin modifiers) by co-expressing these factors with Oct4, Sox2 and c-Myc in mouse embryonic fibroblasts (MEFs) showed that only the Err protein Esrrb was able to induce the formation of ES cell-like cells (Esrrb was selected as a representative member of the Err family, see Table 1). The findings made by the present inventors render previous suggestions more likely that in embryoinic stem cells, Esrrb targets many genes involved in self-renewal, pluripotency and epigenetic regulation of gene expression. This further suggests that Err proteins may mediate reprogramming through up-regulation of embryonic stem (ES) cell-specific genes. The inventors' finding also indicates that it is possible to reprogram somatic cells such as mouse fibroblasts in a manner independent of Klf transcription factors, and it links these nuclear receptors to somatic cell reprogramming.

The present inventors' findings further provide an explanation for previous data in knockdown studies on targets of Oct4 and Nanog. Ivanova, N., et al. (*Nature* (2006) 442, 533-538) identified Esrrb as one of 10 gene product the depletion of which, by means of shRNA, affected self-renewal of mouse ES cells in vitro. Furthermore Esrrb was one of 19 gene products the depletion of which resulted in morphological changes characteristic of differentiating cells and loss of alkaline phosphatase activity (ibid. & Loh, Y.-H., et al., *Nature Genetics* (2006) 38, 4, 431-440). WO 2008/021483 also discloses that mouse embryonic stem cells have been found to lose "sternness" and form colonies of differentiated cells 6 days after treatment with Esrrb siRNA.

The present invention provides methods and uses of preventing, inhibiting, arresting and/or reversing differentiation of a cell. Any cell may be used in the method of the invention. The cell may for instance be a somatic cell or a germline cell. In some embodiments the cell is a hybrid cell of a stem cell and a somatic cell. The cell may be of any origin and of any differentiation status. The cell may for instance be entirely differentiated, to any extent differentiated or undifferentiated. In embodiments where the cell is undifferentiated the method of the invention is typically a method of maintaining pluripotency, including multipotency as well as totipotency—the capability of forming all cell types of the organism—where applicable, and/or self-renewing characteristics of the same (FIG. 1 left hand side). Usually such a cell is an undifferentiated cell, such as a stem cell, e.g. an embryonic stem cell, a trophoblast stem cell and any extraembryonic stem cell, e.g. an adult stem cell. Further examples of an undifferentiated cell include a germ cell, an oocyte, a blastomer, and an inner cell mass cell.

An example of a cell that is a partially differentiated cell is a progenitor cell (FIG. 1, center). A progenitor cell, which may be unipotent or multipotent, has a capacity to differentiate into a specific type of cell and a limited ability of self-renewal, which it cannot maintain. Further examples of a partially differentiated cell include, but are not limited to, a precursor cell, i.e. a stem cell that has developed to the stage where it is committed to forming a particular kind of new blood cell, a lineage-restricted stem cell, and a somatic stem cell. Examples of suitable somatic cells, include, but are not limited to a fibroblast, a myeloid cell, a B lymphocyte, a T lymphocyte, a bone cell, a bone marrow cell, a pericyte, a dendritic cell, a keratinocyte, an adipose cell, a mesenchymal cell, an epithelial cell, an epidermal cell, an endothelial cell, a chondrocyte, a cumulus cell, a neural cell, a glial cell, an astrocyte, a cardiac cell, an esophageal cell, a muscle cell (e.g. a smooth muscle cell or a skeletal muscle cell), a pancreatic beta cell, a melanocyte, a hematopoietic cell, a myocyte, a macrophage, a monocyte, and a mononuclear cell. A somatic cell may be a cell of any tissue, such as for instance skin, kidney, spleen, adrenal, liver, lung, ovary, pancreas, uterus, stomach, colon, small intestine, spleen, bladder, prostate, testicular, thymus, muscle, connective tissue, bone, cartilage, vascular tissue, heart, eye or neural tissue.

The cell may be obtained or derived from any host organism. The cell may be directly taken from a respective host organism in form of a sample such as e.g. a biopsy or a blood sample. It may also have been derived from a host organism and subsequently been cultured, grown, transformed or exposed to a selected treatment. In some embodiments the cell may be included in a host organism. It may for instance be present in the blood or in an organ of the host organism. The host organism from which the cell is derived or obtained may be any organism such as a microorganism, an animal, such as a fish, an amphibian, a reptile, a bird, a mammal, including a rodent species, an invertebrate species, e.g. of the subclass Lissamphibia that includes e.g. frogs, toads, salamanders or newts, or a plant. Examples of mammals include, but are not limited to, a rat, a mouse, a rabbit, a guinea pig, a squirrel, a hamster, a vole, a platypus, a dog, a goat, a horse, a pig, an elephant, a chicken, a macaque, a chimpanzee and a human.

Where the method of the invention is intended to be used for a progenitor cell, i.e. a cell giving rise to a mature somatic cell, any progenitor cell may be used in this method of the invention. Examples of suitable progenitor cells include, but are not limited to, neuronal progenitor cells, endothelial progenitor cells, erythroid progenitor cells, cardiac progenitor cells, oligodendrocyte progenitor cells, retinal progenitor cells, or hematopoietic progenitor cells.

A cell used in a method of the present invention is typically capable of expressing at least one Err protein in that it includes a nucleic acid sequence encoding an Err protein, generally in the form of a functional gene of the Err protein (whether endogenous or heterologous). In some embodiments the cell is capable of expressing all Err proteins. In some embodiments the cell is expressing one or more Err proteins, such as Esrrb, Esrrd and/or Esrrg. In some embodiments the cell is expressing all Err proteins. In some embodiments one or more respective, for instance endogenous, genes encoding an Err protein are functionally active and expressing the Err protein(s). In some embodiments one or more endogenous nucleic acid sequences encoding one or more Err proteins are functionally inactive. In some of these embodiments an Err protein is nevertheless expressed—from a heterologous Err gene. A heterologous gene encoding an Err protein may be introduced by means of recombinant technology, for instance by means of a nucleic acid molecule, typically as a vector carrying an Err protein gene (cf. also below). It may in this regard be advantageous to further use a vector that contains a promoter effective to initiate transcription in the respective host cell (whether of endogenous or heterologous origin). In this regard the present invention also relates to the use of such a nucleic acid molecule, e.g. a respective vector, for increasing the absolute quantity of an Err protein in a cell. The invention also relates to the use of such a nucleic acid molecule, e.g. a respective vector, in the manufacture of an agent, such as a medicament, for modulating the differentiation status of a cell, in particular for effecting de-differentiation of an at least partially differentiated cell or maintaining pluripotency and/or self-renewing characteristics of an undifferentiated cell.

The term "vector" relates to a single or double-stranded circular nucleic acid molecule that can be transfected into cells and replicated within or independently of a cell genome. A circular double-stranded nucleic acid molecule can be cut and thereby linearized upon treatment with restriction enzymes. An assortment of nucleic acid vectors, restriction enzymes, and the knowledge of the nucleotide sequences cut by restriction enzymes are readily available to those skilled in the art. A nucleic acid molecule encoding an Err protein can be inserted into a vector by cutting the vector with restriction enzymes and ligating the two pieces together.

The term "promoter" as used herein, refers to a nucleic acid sequence needed for gene sequence expression. Promoter regions vary from organism to organism, but are well known to persons skilled in the art for different organisms. For example, in prokaryotes, the promoter region contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, and the like.

The term "nucleic acid" as used herein refers to any nucleic acid molecule in any possible configuration, such as single stranded, double stranded or a combination thereof. Nucleic acids include for instance DNA molecules, RNA molecules, analogues of the DNA or RNA generated using nucleotide analogues or using nucleic acid chemistry, locked nucleic acid molecules (LNA), peptide nucleic acid molecules (PNA) and tecto-RNA molecules (e.g. Liu, B., et al., *J. Am. Chem. Soc.* (2004) 126, 4076-4077). A PNA molecule is a nucleic acid molecule in which the backbone is a pseudopeptide rather than a sugar. Accordingly, PNA generally has a charge neutral backbone, in contrast to for example DNA or RNA. Nevertheless, PNA is capable of hybridising at least complementary and substantially complementary nucleic acid strands, just as e.g. DNA or RNA (to which PNA is considered a structural mimic). An LNA molecule has a modified RNA backbone with a methylene bridge between C4' and O2', which locks the furanose ring in a N-type configuration, providing the respective molecule with a higher duplex stability and nuclease resistance. Unlike a PNA molecule an LNA molecule has a charged backbone. DNA or RNA may be of genomic or synthetic origin and may be single or double stranded. Such nucleic acid can be e.g. mRNA, cRNA, synthetic RNA, genomic DNA, cDNA, synthetic DNA, a copolymer of DNA and RNA, oligonucleotides, etc. A respective nucleic acid may furthermore contain non-natural nucleotide analogues and/or be linked to an affinity tag or a label.

Many nucleotide analogues are known and can be used in the method of the invention. A nucleotide analogue is a nucleotide containing a modification at for instance the base, sugar, or phosphate moieties. As an illustrative example, a substitution of 2'-OH residues of siRNA with 2'F, 2'O-Me or 2'H residues is known to improve the in vivo stability of the respective RNA. Modifications at the base moiety include natural and synthetic modifications of A, C, G, and T/U, different purine or pyrimidine bases, such as uracil-5-yl, hypoxanthin-9-yl, and 2-aminoadenin-9-yl, as well as non-purine or non-pyrimidine nucleotide bases. Other nucleotide analogues serve as universal bases. Universal bases include 3-nitro-pyrrole and 5-nitroindole. Universal bases are able to form a base pair with any other base. Base modifications often can be combined with for example a sugar modification, such as for instance 2'-O-methoxyethyl, e.g. to achieve unique properties such as increased duplex stability.

In some embodiments a method or use according to the invention includes increasing the activity of an Err protein, or a functional fragment thereof, in the cell. The respective Err protein may for instance be Esrrb, Esrrd or Esrrg. In some embodiments increasing the activity of the Err protein in the cell includes modulating, such as increasing or reducing, the interaction of the Err protein with a nucleic acid target sequence. Esrra and Esrrb have been found to activate transcription via the estrogen response element and via the palindromic thyroid hormone response element in a constitutively active form, i.e. the absence of a ligand (Xie, W., et al., *Molecular Endocrinology* (1999) 13, 2151-2162). Esrrg1 has been shown to activate response elements such as sft4, SF-1RE, and TREpal (Sanyal, S., et al., *Molecular Endocrinology* (2004) 18, 2, 312-325) as well as an ERR regulatory element in the promoter of DAX-1 (dosage-sensitive sex reversal, adrenal hypoplasia critical region, on chromosome X, gene 1), (NR0B1) (Park, Y.-Y., et al., *Nucleic Acids Research* (2005) 33, 21, 6756-6768), an orphan nuclear receptor. Nuclear immunoreactivity of DAX-1 was detected in breast cancer tissues and overexpression of Esrrg was observed in three out of nine cases (ibid.). Esrrg2 was found to bind to e.g. the DR-0 element of the human PDGF promoter and an extended half-site of the lactoferrin promoter (Hentschke, M, et al., *Eur. J. Biochem.* (2002) 269, 16, 4089-4097).

In some embodiments increasing the activity of the Err protein in the cell includes forming a complex between the Err protein and a further protein or enhancing the formation of such a complex. Typically the protein with which the Err protein forms a complex is also a nuclear protein. In this regard other nuclear receptors, GRIP 1, and—to a smaller extent—SRC-1a and ACTR were found to act as transcriptional coactivators of Esrra and Esrrb (ibid). PPARγ coactivator (PGC1a) has furthermore been shown to function as an activating factor of Esrrb and Esrrg (see e.g. Zuercher, W. J., et al., *Journal of Medicinal Chemistry* (2005) 48, 3107-3109, and references cited therein). In addition to PGC-1a and PGC-1β (Hentschke et al., 2002, supra), further illustrative examples of suitable activators of Esrrg are P160 coactivators, such as transcription intermediary factor 2/glucocorticoid receptor interaction protein 1, steroid receptor coactivator 1, amplified in breast cancer 1, and RAP250/activating signal cointegrator 2 (ASC2) (see e.g. Sanyal et al., 2004, supra). It is noted in this regard that Esrrg activity has furthermore been shown to depend on the response elements that it binds (ibid.). One or more activators of Esrrg2 are furthermore included in serum and reticulocyte lysate (Hentschke et al., 2002, supra).

In some embodiments increasing the activity of the Err protein in the cell includes forming a complex between the Err protein and a compound. Suitable examples of a compound activating an Err protein include, but are not limited to, a peptide, a peptoid, an inorganic molecule and a low molecular weight organic molecule.

A respective low molecular weight organic molecule suitable as an agonist ligand for Esrrb may for instance be a 4-hydroxybenzoic acid aryl hydrazide, a flavone phytoestrogen or an isoflavone phytoestrogen. The aryl moiety of a corresponding 4-hydroxybenzoic acid aryl hydrazide is typically a 6-membered ring, i.e. a benzene derivative. An illustrative example of a 4-hydroxybenzoic acid aryl hydrazide is 4-hydroxybenzoic acid 2-[[4-(diethylamino)phenyl]methylene]hydrazide (Chemical Abstracts No 95167-41-2), also known as DY131 or GSK 9089 (Yu, D., *Bioorganic & Medicinal Chemistry Letters* (2005) 15, 1311-1313; Zuercher, W. J., et al., *Journal of Medicinal Chemistry* (2005) 48, 3107-3109; US patent application 2006/0189825). A further illustrative example is 4-hydroxybenzoic acid [[4-(1-methylethyl)phenyl]methylene]hydrazide (CAS-No 101574-65-6), also known as GSK 4716, which has likewise been found to activate Esrrb. Examples of suitable flavone and isoflavone phytoestrogens include, but are not limited to, Genistein (5,7,4'-trihydroxyisoflavone), Daidzein (7,4'-dihydroxyisoflavone), Biochanin A (5,7-dihydroxy-4'-methoxyisoflavone), which have, as well as to a smaller extent, 6,3', 4'-trihydroxyflavone (flavone), also been reported to activate Esrrb (Suetsugi, M., et al., *Molecular Cancer Research* (2003) 1, 981-991).

For Esrra and Esrrg so far no compounds have been identified that act as activators as such, in particular as agonists. However, replacement of an inverse agonist—such compounds with an overall inhibitory effect are for instance known for both Esrra and Esrrg—may be taken as an activation of the respective Err protein. As an illustrative example, bisphenol A as well as 4-α-cumylphenol activate Esrrg by replacing 4-hydroxytamoxifen, which deactivates Esrrg (Matsushima et al., 2008, supra). Bisphenol A has further been denoted an inverse antagonist of Esrrg as it is capable of increasing Esrrg activity (supra, Liu et al., 2007, supra). Furthermore, it can be expected that in view of recent crystal data (e.g. Kallen, J., et al., *J. Biol. Chem.* (2007) 282, 23, 23231-23239) activators can be identified in the future. Such compounds may then be used in a method according to the present invention.

In some embodiments increasing the activity of the Err protein in the cell includes forming a complex between the Err protein, a further protein and a compound. The further protein and the compound may be as defined above. As illustrative examples, in the presence of PPARγ coactivator (PGC1a) the compounds 4-hydroxybenzoic acid benzylidene hydrazide (DY159), 4-hydroxybenzoic acid (3-methyl-benzylidene)hydrazide (DY162), 4-hydroxybenzoic acid (4-methyl-benzylidene)hydrazide (DY163) and 4-hydroxybenzoic acid (5-ethyl-thiophen-2-ylmethylene)hydrazide (DY164) have been found to activate Esrrb (US 2006/0189825). In this regard the present invention also relates to the use of a compound as described above, e.g. one of the above named examples, for increasing the activity of an Err protein in a cell. The invention also generally relates to the use of a compound for increasing the activity and/or the absolute quantity of an Err protein in a cell. The invention also relates to the use of such a compound in the manufacture of an agent, such as a medicament, for increasing the differentiation status of a cell.

In some embodiments the activity and/or the cellular amount of the Err protein is altered by an alteration of a posttranslational modification such as phosphorylation (Tremblay, A. M., et al., *Mol. Endocrinol.* (2008) 22, 3, 570-584). In some embodiments the activity and/or the amount of the Err protein in the cell is modulated by sumoylation, attachment of the small ubiquitin-related modifier (SUMO) protein (ibid.). Esrra and Esrrg have been shown to be sumoylated and thereby their transcriptional activity negatively modulated (ibid.). Thus in some embodiments of the method of the invention increasing the activity of the Err protein in the cell includes allowing an alteration of a posttranslational modification to occur, such as an alteration of phosphorylation and/or sumoylation. In typical embodiments sumoylation only occurs on the corresponding phosphorylated Err protein.

In some embodiments the cell is not expressing the one or more Err proteins of interest, or it is not expressing any Err protein. In such embodiments the method of the invention may include activating one or more endogenous genes encoding one or more Err proteins. In some embodiments the method of the invention includes introducing into the cell a nucleic acid molecule, typically a heterologous nucleic acid molecule (supra), encoding an Err protein capable of allowing expression of the same in the cell. The method in such embodiments further includes expressing the heterologous Err protein.

A method according to the invention may further include measuring the expression of the respective gene. This can for instance be achieved by determining the number of RNA molecules transcribed from a gene that is under the control of the respective promoter. A method commonly used in the art is the subsequent copy of RNA to cDNA using reverse transcriptase and the coupling of the cDNA molecules to a fluorescent dye. The analysis is typically performed in form of a DNA microarray. Numerous respective services and kits are commercially available, for instance GeneChip® expression arrays from Affymetrix. Other means of determining gene expression of an Err protein include, but are not limited to, oligonucleotide arrays, and quantitative Real-time Polymerase Chain Reaction (RT-PCR).

In some embodiments it may be advantageous or desired to calibrate gene expression data or to rate them. Thus, in some embodiments the methods of the invention additionally include the comparison of obtained results with those of one or more control measurements. Such a control measurement may include any condition that varies from the main measurement itself. It may include conditions of the method under which for example no expression of the respective gene occurs. A further means of a control measurement is the use of a mutated form of a respective gene, for example a gene not encoding an Err protein, or encoding a non-functional Err protein.

The Err protein, the amount or activity of which is increased, may be any variant, isoform, allel etc. of the respective Err protein. Illustrative examples of Esrrb are the proteins of the GenPept accession Nos AAH44858 (mouse), AAI11278 (bovine), AAI31518 (human), 095718 (human), NP_001008516 (rat), XP_001162698 (chimpanzee), XP_001100608 (Macaca mulatta), XP_001519435 (platypus), XP_001491623 (horse), XP_001235147 (chicken), XP_001333980 (zebrafish), ABF65992 (southern vole), XP_001928086 (pig), as well as hERRb2-Δ10 and short-form hERRβ, both described by Zhou et al. (*J. Clin. Endocrinol. & Metab.* (2006) 91, 2, 569-579). Illustrative examples of Esrrg are the human protein of UniProtKB/Swiss-Prot accession No. P62508, the orangutan protein of UniProtKB/Swiss-Prot accession No. Q5RAM2, the mouse protein of UniProtKB/Swiss-Prot accession No. P62509, the rat protein of UniProtKB/Swiss-Prot accession No. P62510, the *Xenopus* protein of UniProtKB/TrEMBL accession No. A41IT9, the zebrafish protein of UniProtKB/TrEMBL accession No. Q6Q6F4 and the horse proteins of GenPept accession Nos XP_001489640, XP_001489725, XP_001489702 and XP_001489611.

Illustrative examples of Esrra are the human protein of UniProtKB/Swiss-Prot accession No. P11474, the dog protein of UniProtKB/Swiss-Prot accession No. Q6QMY5, the mouse protein with UniProtKB/Swiss-Prot accession No. 008580, the rat protein with UniProtKB/Swiss-Prot No. Q5QJV7, the *Xenopus* protein of UniProtKB/TrEMBL accession No. AOJM86 and the zebrafish protein of UniProtKB/TrEMBL accession No 042537.

The methods and uses according to the present invention may further include assessing the amount or the activity of one or more Err proteins, or of the corresponding functional fragment(s) of the Err protein(s) in the cell. The amount or the activity of any Err protein of interest may be assessed.

The amount of an Err protein in a cell may for example be assessed by means of an antibody such as an immunoglobulin, which may be conjugated to a label. In case of the cell being an isolated cell or a microorganism, an intracellular immunoglobulin may be introduced into the cell, for instance following permeabilisation of the cell membrane. The detection may then be carried out in vivo or ex vivo. In some embodiments the detection may be carried out in vitro, for example on a cell extract or cell lysate. Such a technique may include electrophoresis, HPLC, flow cytometry, fluorescence correlation spectroscopy or a modified form or a combination of these techniques.

The term "antibody" generally refers to an immunoglobulin, a fragment thereof or a proteinaceous binding molecule with immunoglobulin-like functions. Examples of (recombinant) immunoglobulin fragments are Fab fragments, Fv fragments, single-chain Fv fragments (scFv), diabodies, triabodies (Iliades, P., et al., *FEBS Lett* (1997) 409, 437-441), decabodies (Stone, E., et al., *Journal of Immunological Methods* (2007) 318, 88-94) and other domain antibodies (Holt, L. J., et al., *Trends Biotechnol.* (2003), 21, 11, 484-490). An example of a proteinaceous binding molecule with immunoglobulin-like functions is a mutein based on a polypeptide of the lipocalin family (WO 2003/029462; WO 2005/019254; WO 2005/019255; WO 2005/019256; Beste et al., *Proc. Natl. Acad. Sci. USA* (1999) 96, 1898-1903). Lipocalins, such as the bilin binding protein, the human neutrophil gelatinase-associated lipocalin, human Apolipoprotein D, human tear lipocalin, or glycodelin, posses natural ligand-binding sites that can be modified so that they bind to selected small protein regions known as haptens. Other non-limiting examples of further proteinaceous binding molecules so-called glubodies (see WO 96/23879), proteins based on the ankyrin scaffold (Mosavi, L. K., et al., *Protein Science* (2004) 13, 6, 1435-1448) or the crystalline scaffold (WO 2001/04144), the proteins described by Skerra (*J. Mol. Recognit.* (2000) 13, 167-187), AdNectins, tetranectins, avimers and peptoids. Avimers contain so called A-domains that occur as strings of multiple domains in several cell surface receptors (Silverman, J, et al., *Nature Biotechnology* (2005) 23, 1556-1561). Adnectins, derived from a domain of human fibronectin, contain three loops that can be engineered for immunoglobulin-like binding to targets (Gill, D. S. & Damle, N. K., *Current Opinion in Biotechnology* (2006) 17, 653-658). Tetranectins, derived from the respective human homotrimeric protein, likewise contain loop regions in a C-type lectin domain that can be engineered for desired binding (ibid.). Peptoids, which can act as protein ligands, are oligo(N-alkyl) glycines that differ from peptides in that the side chain is connected to the amide nitrogen rather than the α carbon atom. Peptoids are typically resistant to proteases and other modifying enzymes and can have a much higher cell permeability than peptides (see e.g. Kwon, Y.-U., and Kodadek, T., *J. Am. Chem. Soc.* (2007) 129, 1508-1509). Where desired, a modifying agent may be used that further increases the affinity of the respective moiety for any or a certain form, class etc. of target matter.

Assessing the activity of an Err protein may include a measurement of the binding of the protein to nucleic acid target sequences. Such measurements may for instance rely on spectroscopic, photochemical, photometric, fluorometric, radiological, enzymatic or thermodynamic means both in vivo and in vitro. An example for a spectroscopic detection method is fluorescence correlation spectroscopy (see e.g. Haustein, E., & Schwille, P., *Annu. Rev. Biophys. Biomol. Struct.* (2007) 151-169). A photochemical method is for instance photochemical cross-linking. The use of photoactive, fluorescent, radioactive or enzymatic labels respectively are examples for photometric, fluorometric, radiological and enzymatic detection methods. As an illustrative example, as fluorophores also quantum dots may be employed, including in in-vivo measurements (see e.g. Lidke, D. S., et al., *Current Protocols in Cell Biology* (2007) 25.1.1-25.1.18, doi: 10.1002/0471143030. cb2501s36). A further illustrative example of the use of fluorescence in vivo is employing the yellow fluorescent protein in the bimolecular fluorescence complementation method. A general overview on the use of fluorescent probes has been given by Xie et al. (*Annu. Rev. Biophys.* (2008) 37, 417-44). An example for a thermodynamic detection method is isothermal titration calorimetry. Yet another example of a suitable method of measuring the binding of an Err protein to a nucleic acid sequence is a surface plasmon resonance technique such as localized surface plasmon resonance (e.g. Endo, T., et al., *Analytica Chimica Acta* (2008) 614, 2, 182-189). Some of these methods may include additional separation techniques such as electrophoresis or HPLC. In detail, examples for the use of a label comprise a compound as a probe or an immunoglobulin with an attached enzyme, the reaction catalysed by which leads to a detectable signal. An example of a method using a radioactive label and a separation by electrophoresis is an electrophoretic mobility shift assay.

In some embodiments a method according to the invention includes assessing the differentiation status of a cell. The differentiation status of a cell can for example be assessed under a microscope based on the phenotype displayed by the cell. An experienced artisan is able to assess minute changes in the differentiation status by monitoring a cell's phenotype. The cell's phenotype is also reflected by a cell's macromolecular content. Changes in this content thus indicate a change of differentiation status. Raman microspectroscopy or FT-IR spectroscopy are illustrative examples of suitable techniques for assessing the differentiation status in this regard. Ami et al. (*Biochimica et Biophysica Acta* (2008) 1783, 98-106) have for example recently demonstrated FT-IR spectroscopy techniques including assessing total protein expression and detection of nucleic acid infrared bands for monitoring embryonic stem cell differentiation. By the same techniques dedifferentiation of a cell can likewise be assessed.

A further example of a technique of assessing the differentiation status of a cell is assessing the presence of a marker of the differentiation status of a cell. Such a marker is typically a cellular protein. To qualify as a differentiation marker a protein may be only present in detectable amounts during a certain differentiation status of a cell. Alternatively the marker may be present in a few selected phases characterizing a certain differentiation status of a cell. In this case a combination of different markers, each with a different profile with regard to the differentiation status where it is expressed, can be used to assess the differentiation status of a cell. If for example a first marker indicates a stem cell or a progenitor cell and a second marker indicates a progenitor cell or a fibroblast, the presence of both markers may indicate a progenitor cell. In a further alternative a protein may be present in only particularly high or low amounts during certain stages, i.e. at a certain cell differentiation status. A combination of a number of markers with different characteristics in this regard can again be used to assess the differentiation status of a cell. Generally it is advantageous to select a combination of several markers for assessing the differentiation status of a cell. The presence of a marker protein may be detected on the protein level, for example by means of an antibody (supra), or it may be assessed based on the expression level of the marker protein. Regardless of the protein's half life, the expression of a certain marker protein is generally a suitable indicator of the differentiation status of the respective cell. Examples of proteins, the amount or the expression of which may be assessed as a marker of the differentiation status of a cell, include, but are not limited to Nanog, Oct4, Sox2, Sall4, Tc11, Tbx3, Eras, Klf2, Klf4, Klf5, Baf250a, BC031441, Eno3, Etv5, Gm1739, Gtf2h3, Hes6, Jub, Mtf2, Myod1, Nmyc1, Notch4, Nr5a2, Nrg2, Otx2, Rab2b, Rbpsuh, Rest, Stat3, Utf1, Tcfap2c and Zfp553, or the methylation status of the promoter of one of Nanog, Oct4, Sox2, Sall4, Tc11, Tbx3, Eras, Klf2, Klf4, Klf5, Baf250a, BC031441, Eno3, Etv5, Gm1739, Gtf2h3, Hes6, Jub, Mtf2, Myod1, Nmyc1, Notch4, Nr5a2, Nrg2, Otx2, Rab2b, Rbpsuh, Rest, Stat3, Utf1, Tcfap2c and Zfp553. The expression of a plurality of such markers may be carried out using standard techniques such as microarray hybridization. An example of a microarray that can be used for expression profiling in quantitative terms can be found in European patent application EP 1 477 571.

In some embodiments assessing the differentiation status of a cell includes assessing the amount and/or activity over a period of time. As an example, the cells may, for instance optically be assessed, continuously. As a further example, after selected time intervals an assessment of the cell may be performed. Assessing the differentiation status of a cell may further include a control measurement. The control measurement may include comparable cells, for instance of the same origin, in which the amount or the activity of an Err protein, or a functional fragment thereof, in the cell is not being increased—or in which it is generally not being modulated. For such a control measurement conditions may be selected, under which the amount or the activity of an Err protein is known to be unaffected. Conditions may also be selected for a respective control measurement in such a way that the amount or the activity of an Err protein is prevented from being increased, or from generally being changed. This control measurement may for instance be carried out at about the same time, including simultaneously, as the assessment of the cell is performed, in which the amount and/or the activity of one or more Err proteins, or (a) functional fragment(s) of one or more Err proteins, is being increased.

In some embodiments a pre-defined threshold value is set to define differentiation and de-differentiation, respectively. If the two assessments, i.e. "sample", in which the amount and/or activity of the Err protein is increased, and "control" measurement, differ in such a way that the difference between the determined values that indicate/characterize the differentiation status of a cell is greater than the pre-defined threshold value, dedifferentiation has been achieved. As an illustrative example, the expression of a marker protein may be used to assess the differentiation status of a cell. The expression of the marker protein may indicate dedifferentiation of a cell of the selected cell type. The control measurement may be used to ensure that fluctuations in expression are taken into consideration if any should occur under the selected conditions. If the difference in expression of the marker protein between the "sample" (supra) and the "control" measurement exceeds the pre-defined threshold value, it is concluded that de-differentiation in the "sample" has been effected.

Further suitable methods of evaluating de-differentiated cells include the use of undifferentiated control cells and monitoring the cell's phenotype as for example described in US patent application US 2008/0076176. Pluripotency may for instance be evaluated by the ability of cells to form a chimera, a blend of cells from two or more organisms, after combining the respective stem cells or stem-like cells with the blastocyst of an embryo that subsequently forms a completely integrated organism from the cell mixture. A further way of evaluating pluripotency is the injection of the respective stem cells beneath the skin of a mouse where they can form a teratoma. A further evaluation method is tetraploid complementation, an in vivo test that measures the pluripotency of corresponding cells by their injection into 4N embryos that are incapable of further differentiation. The resultant normal 2N embryo continues to develop from the imported pluripotent cells.

Once optimizations in practical terms, such as identification of the most suitable vectors, have been carried out in more detail, cells obtained by a method of the invention, e.g. induced stem cells or progenitor cells, may readily be used as alternatives to presently available cells. Recently it has for instance been demonstrated that genome-integrating viruses are not required to obtain induced pluripotent stem cells. As one alternative nonintegrating adenoviruses transiently expressing Oct4, Sox2, Klf4, and c-Myc have been used by Stadtfeld et al. (*Science* (2008) doi: 10.1126/science.1162494), as another alternative repeated transfection of only one plasmid containing the cDNAs of Oct3/4, Sox2, and Klf4, together with a c-Myc expression plasmid, has been used by Okita et al. (*Science* (2008) doi: 10.1126/science.1164270).

Where the method of the invention has been used to dedifferentiate a cell to a sufficiently undifferentiated cell state, the obtained cells, typically stem-like cells, may for instance be used to obtain any desired differentiated cell type. Hence, a method according to the invention may serve a large variety of therapeutic usages. Such cells may for example be used in regenerative medicine with the advantage that cells from the same individual can be used to provide cells of a selected cell type. As an illustrative example, human hematopoietic stem cells may be used in medical treatments requiring bone marrow transplantation. Cells obtained according to the invention may be put to use in treating many physiological conditions and diseases, e.g., neurodegenerative diseases such as multiple sclerosis, late stage cancers such as ovarian cancer and leukemia, as well as diseases that compromise the immune system, such as HIV infection ("AIDS"). Further examples of physiological conditions that may be treated include, but are not limited to, spinal cord injuries, multiple sclerosis, muscular dystrophy, diabetes, liver diseases, i.e., hypercholesterolemia, heart diseases, cartilage replacement, burns, foot ulcers, gastrointestinal diseases, vascular diseases, kidney disease, urinary tract disease, and aging related diseases and conditions. Such cells may also be used in the formation of one or more cell lines.

Methods of the invention may also be used for research purposes, for example by reversibly de-differentiating and differentiating cells, in some embodiments also in the presence of compounds of interest. In this regard cells obtained by a method of the invention may also be used to in vitro, ex vivo or in vivo model cells entering a certain state, e.g. a disease state or cells in a certain state, e.g. a disease state. Such cells may also be used to study the development of an organism such as an animal including a human. Where a method according to the invention is used to generate induced pluripotent stem cells, disease specific pluripotent cell lines may be generated analogous to the technique described by Park et al. (*Cell* (2008) 134, 877-886).

In some embodiments a method according to the invention is a method of maintaining pluripotency and/or self-renewing characteristics of an undifferentiated cell. While stem cells such as embryonic stem cells can be differentiated in a controlled fashion, for instance into neurons in the presence of nerve growth factor and retinoic acid (Schuldiner et al. *Br. Res.* (2001) 913, 201-205), their ability to readily differentiate has posed a major practical challenge. In order to maintain embryonic stem cells in a pluripotent state, their differentiating during handling and growing in culture has to be prevented. For this reason they are traditionally cultured in the presence of fetal calf serum on a layer of feeder cells (see e.g. U.S. Pat. No. 5,843,780 and No. 6,090,622) or in fibroblast-conditioned medium (CM). Nevertheless, even under carefully controlled conditions embryonic stem cells may undergo spontaneous differentiation during in-vitro propagation. Leukaemia inhibitory factor (LIF), a factor mediating self-renewal in mouse embryonic stem cells, has also been found to inhibit differentiation of mouse embryonic stem cells, but it does not replace the role of feeder cells in preventing differentiation of human embryonic stem cells. Therefore, those skilled in the art will appreciate the method for modulating, including maintaining, pluripotency and/or self-renewing characteristics of a stem cell as a significant improvement.

Adult stem cells, although not pluripotent like embryonic stem cells, have been shown to be capable of self-renewal and to be of a plasticity rendering their developmental capabilities comparable to those of the more immature pluripotent embryonic stem cells. As an example, an adult stem cell is able to differentiate into a cell lineage different from its tissue of origin.

The method of maintaining pluripotency and/or self-renewing characteristics of the present invention is suitable for any stem cell, progenitor cell, teratoma cell or any cell derived therefrom. Typically, a respective cell is able to express an Err protein. As an illustrative example, any pluripotent human embryonic stem cell or a respective cell line may be used in the respective method. Means of deriving a population of such cells are well established in the art (cf. e.g. Thomson, J. A., et al., *Science* [1998] 282, 1145-1147 or Cowan, C. A., et al. *N. Engl. J. Med.* [2004] 350, 1353-1356). Furthermore, at least 78 independent human embryonic stem cell lines are for example known to exist, of which at least 21 cell lines are available for research purposes (see e.g. the NIH Human Embryonic Stem Cell Registry at http://stemcells.nih.gov/research/registry/eligibilityCriteria.asp), such as GE01, GE09, BG01, BG02, TE06 or WA09. Embryonic, including human embryonic stem cells may for instance be derived from morula, later blastocyst stage embryos, single blastomers or parthenogenetic embryos. Pluripotent fetal stem cells as well as progenitor cells may be isolated from a fetus. Pluripotent fetal stem cells can also be isolated from extra-fetal tissues usually discarded at birth. Adult stem cells may for instance be isolated from tissue such as neural tissue (Chojnacki, A., & Weiss, S., *Nature Protocols* (2008) 3, 935-940) or adipose tissue (Bunnell, B. A., et al., *Methods in stem cell research* (2008) 45, 2, 115-120), from spermatogonial cells of testis (e.g. Conrad, S., et al., *Nature* (2008) doi: 10.1038/nature07404), from teeth, from blood from the placenta and umbilical cord left over after birth, or from myofibers, to which stem cells and progenitor cells are associated as so called "satellite cells" (Collins, C. A., et al. *Cell* [2005] 122, 289-301, see also Rando, T. A., *Nature Medicine* [2005] 11, 8, 829-831). Progenitor cells may also be isolated from blood and from a variety of tissues, such as neural tissue, the subventricular zone, pancreas, the retina, the periosteum or endothel.

The term "stem cell" as used herein refers to any stem cell and also includes a so called cancer stem cell. Many types of cancer have been found to include such cancer stem cells, which are characterized by their self-renewing capacity and differentiation ability. A wide range of studies show that most cancers are clonal and may represent the progeny of a single cancer stem cell endowed with the capacity to maintain tumour growth. Krivtsov et al. (*Nature* (2006) 442, 818-822) have for example purified a cell population highly enriched for progenitor-derived leukaemia stem cells and characterised them by gene expression profiling. They report that these cells resemble the progenitor from which they arose, but express a self-renewal-associated programme normally expressed in haematopoietic stem cells (ibid.).

In some embodiments a method according to the invention includes administering a compound that modulates the expression and/or the activity of an Err protein to the cell or to the host organism in which the cell is included. The term "administering" relates to a technique of incorporating a compound into a cell or tissue of an organism.

The compounds described herein, as well as compounds identified by a method of the invention, can be administered to a cell, an animal or a human patient per se, or in a pharmaceutical composition where they are mixed with other active ingredients or suitable carriers or excipient(s), including stabilizers. Such carriers, excipients or stabilizers are usually pharmaceutically acceptable in that they are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

Suitable routes of administration may, for example, include depot, oral, rectal, transmucosal, or intestinal administration; parenteral delivery, including intramuscular, subcutaneous, intravenous, intramedullary injections, as well as intrathecal, direct intraventricular, intraperitoneal, intranasal, or intraocular injections. The compound may also be administered in a local rather than systemic manner, for example, via injection of the compound directly into a tissue, for example in a depot or sustained release formulation.

Furthermore, one may administer the drug in a targeted drug delivery system, for example, in a liposome coated with tumor-specific antibody. The liposomes will be targeted to and taken up selectively by the tissue that includes the cell or cells of interest.

A composition that includes a compound described above of may be manufactured in a manner that is itself known for pharmaceutical compositions, e.g., by means of conventional mixing, dissolving, granulating, dragee-making, levigating, emulsifying, encapsulating, entrapping or lyophilizing processes. A composition for use in accordance with the present invention thus may be formulated in conventional manner using one or more physiologically acceptable carriers including excipients and auxiliaries that facilitate processing of the active compounds into preparations that can be used pharmaceutically. Proper formulation is dependent upon the route of administration chosen.

For injection, the compound may be formulated in aqueous solutions, for instance in physiologically compatible buffers such as Hanks's solution, Ringer's solution, or physiological saline buffer. For transmucosal administration, penetrants appropriate to the barrier to be permeated are used in the formulation. Such penetrants are generally known in the art. For oral administration, the compound can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated.

A preparation for oral use can be obtained by adding a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethyl-cellulose, and/or polyvinylpyrrolidone (PVP). If desired, a disintegrating agent may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

A preparation that includes a compound described above can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoro-methane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compound may be formulated for parenteral administration by injection, e.g., by bolus injection or continuous infusion. Formulations for injection may be presented in unit dosage form, e.g., in ampules or in multi-dose containers, with an added preservative. A erspective composition may take such forms as suspensions, solutions or emulsions in oily or aqueous vehicles, and may contain formulatory agents such as suspending, stabilizing and/or dispersing agents.

An illustrative example of a suitable formulation for parenteral administration is an aqueous solution of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

The active ingredient may also be in powder form for constitution with a suitable vehicle, e.g., sterile pyrogen-free water, before use. The compounds may also be formulated in rectal compositions such as suppositories or retention enemas, e.g., containing conventional suppository bases such as cocoa butter or other glycerides.

In addition to the formulations described previously, the compound may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

In a further aspect the invention provides a method of identifying a compound capable of effecting de-differentiation of a cell. Such methods may include allowing an interaction, including the formation of a complex, between the compound and the Err protein. In one embodiment the method may include determining whether the compound alters, such as prevents, reduces or enhances, the formation of a complex between an Err protein and one or both of Nanog and Oct4. In a further embodiment the method includes determining whether the compound modulates, including enhances, reduces or prevents, the transcription factor activity of the Err protein.

In some embodiments a respective method includes introducing the compound into a cell capable of expressing one or more Err proteins, or (a) functional fragment(s) of one or more Err protein(s), and determining the expression of the Err protein(s) (see above for details). An increased expression of a respective Err protein is an indication that the corresponding compound is capable of effecting de-differentiation of an at least partially differentiated cell or of maintaining pluripotency and/or self-renewing characteristics of an undifferentiated cell.

The formation of this complex may be carried out using a suitable spectroscopic, photochemical, photometric, fluorometric, radiological, enzymatic or thermodynamic method. Illustrative examples are the detection by surface plasmon resonance (e.g. Biacore®-technology), nuclear magnetic resonance or crystallization and subsequent X-ray analysis. An example of a spectroscopic detection method is fluorescence correlation spectroscopy (Thompson, N. L., et al. *Curr. Opin. Struct. Biol.* [2002] 12, 5, 634-641). A photochemical method is for instance photochemical cross-linking. The use of photoactive, fluorescent, radioactive or enzymatic labels respectively are examples for photometric, fluorometric, radiological and enzymatic detection methods (see also above).

In some embodiments such a method is an in-vitro method. It may include contacting the compound, an Err protein, or a functional fragment thereof, and Nanog or Oct4, or all three proteins. In such a method it is generally determined whether the compound is capable of modulating the formation of a complex between the Err protein and at least one of Nanog and Oct4. Where the compound reduces or prevents the formation of such a complex the compound is a candidate molecule that may be suitable of effecting differentiation. Where the compound increases or facilitates the formation of such a complex this indicated that the compound is capable of effecting de-differentiation of an at least partially differentiated cell or of maintaining pluripotency and/or self-renewing characteristics of an undifferentiated cell.

The above described embodiment of an in-vitro method may include adding to a test tube a compound that is suspected to be capable of modulating the complex formation of an Err protein, or a functional fragment thereof, and at least one of Nanog and Oct4. The method may further include adding the Err protein, or a functional fragment thereof, to the test tube. The method may also include adding Nanog or Oct4 to the test tube. In some embodiments both Nanog and Oct4 are added to the test tube. They may be added together or sequentially. They may also be added before, together with or after adding the Err protein to the test tube. Further the method may include allowing the formation of a complex between the Err protein and Nanog and/or Oct4. The method also includes detecting the formation of this complex. As explained above, the formation of this complex may be carried out using a suitable spectroscopic, photochemical, photometric, fluorometric, radiological, enzymatic or thermodynamic method.

The invention is further illustrated by the following non limiting examples. As one of ordinary skill in the art will readily appreciate from the disclosure of the present invention, other compositions of matter, means, uses, methods, or steps, presently existing or later to be developed that perform substantially the same function or achieve substantially the same result as the corresponding exemplary embodiments described herein may likewise be utilized according to the present invention.

EXAMPLES

Cell Culture and Transfection

Mouse ES cells were cultured on gelatin-coated dishes in Dulbecco's modified Eagle medium (DMEM; GIBCO), supplemented with 15% heat-inactivated fetal bovine serum (FBS; GIBCO), 0.055 mM β-mercaptoethanol (GIBCO), 2 mM L-glutamine, 0.1 mM MEM nonessential amino acid, 5,000 units/ml penicillin/streptomycin and 1,000 units/ml of LIF (Chemicon) and passage every 2~3 days. Reprogrammed cells, V6.4 and R1 mouse ES cells were cultured on mitomycin C-treated mouse embryonic fibroblast (MEF) feeders in the same ES cell medium and passage every 2~3 days. MEFs were isolated from 13.5 d.p.c embryos by dissociation with 0.05% trypsin at 37° C. for 10 min and cultured in 15% FBS/DMEM containing 200 µg/ml gentamicin. In this study, we used MEFs within 5 passages to avoid replicative senescence. MEFs from CD1, B6, 129/B6, Actin-GFP, Actin-GFP/CD1, Pou5fl-GFP/B6 mice have been used for the iPS induction in this study. Transfection of shRNA and over-expression plasmids was performed using Lipofectamine 2000 (Invitrogen) according to manufacturer's instructions. Briefly, 1.5 µg of plasmids were transfected into ES cells on 60 mm plates for RNA and protein extraction. Detection of alkaline phosphatase, which is indicative of the nondifferentiated state of ES cells, was carried out using a commercial ES Cell Characterization Kit from Chemicon. Puromycin (Sigma) selection was introduced 1 day after transfection at a concentration of 0.8 µg/ml, and maintained for 2 to 6 days prior to harvesting.

RNA Extraction, Reverse Transcription and Quantitative Real-Time PCR

Total RNA was extracted using TRIzol Reagent (Invitrogen) and purified with the RNAeasy Mini Kit (Qiagen). Reverse transcription was performed using SuperScript II Kit (Invitrogen). DNA contamination was removed by DNase (Ambion) treatment, and the RNA was further purified by an RNAeasy column (Qiagen). Quantitative PCR analyses were performed in real time using an ABI PRISM 7900 Sequence Detection System and SYBR Green Master Mix as described. For all the primers used, each gave a single product of the right size. In all our controls lacking reverse transcriptase, no signal was detected. Each RNAi experiment was repeated at least 3 times with different batches of ES cells. The sequences targeted by Esrrb shRNA are as described in Loh et al (2006, supra).

Mice

Wild type CD1 mice, B6 mice, Actin-EGFP transgenic mice and Pou5fl-EGFP transgenic mice (Jackson's Lab, Stock No 003516 and 004654 respectively) were used for MEF isolation. B6 mice were used for microinjection.

Retrovirus Packaging and Infection

CDSs of Esrrb and other factors were amplified from mouse ES cells by PCR and cloned into MMLV based pMXs retroviral vector. The retroviruses were generated as described by Takahashi and Yamanaka (2006, supra). To induce iPS cells, equal amounts of viruses encoding different factors were applied on MEF at 50~70% confluence in 15% FBS/DMEM containing 6 ng/ml polybrene. After 24 hrs, medium were changed to fresh and in the following day (2 dpi) cells were split as 1:6~1:20 on MEF feeder. The culture was then maintained for 11~24 days in mouse ES cell culture medium.

Immunoflourescence & Immunochemistry

ES cells or reprogrammed cells cultured on MEF feeders in glass bottom dish or on gelatinized cover slips were fixed with 4% PFA/PBS. After the permeablization in 1% triton-X 100/PBS for 30 min, Nanog was stained with 1:20 Anti-Nanog (RCAB0002 PF, CosmoBio) followed by 1:300 Alexa Flour 568 conjugated anti-rabbit (Invitrogen). SSEA1 was stained directly with 1:200 monoclonal anti-SSEA1 (MAB4301, Chemicon) followed by 1:2000 Alexa Flour 546 conjugated anti-mouse IgM. DAPI or Hoechst (Invitrogen) were used for counterstaining. For immunochemistry analysis, E9.5 embryos were fixed in 4% PFA at 4° C. for overnight and embedded in paraffin. After sectioning, GFP was stained with 1:200 anti-GFP (sc-9996, Santa Cruz) followed by HRP-conjugated anti-mouse (VECTASTAIN ABC kit, Vector), and then developed with DAB (3,3'-Diaminobenzidine). Nuclei were counterstained with Heamotoxylin.

G-Band Karyotyping

Cells were treated with colcemid for mitotic arrest and harvested by standard hypotonic treatment and methanol:acetic acid (3:1) fixation. Slides were prepared by standard air drying method and G-band karyotype was performed.

Microinjection iPS cells were resuspended in M2 medium (which is available from SAFC Biosciences, Catalogue number 5170C and which is a modification of M16 Embryo Culture Medium) and injected into 8 cell stage B6 mouse embryos. The embryos were then allowed to develop to test for the ability of iPS cells to incorporate into the animals.

Chromatin Immunoprecipitation (ChIP) Assay

ChIP assays were carried out as previously described. Briefly, cells were cross-linked with 1% formaldehyde for 10 min at room temperature and formaldehyde was then inactivated by the addition of 125 mM glycine. Chromatin extracts containing DNA fragments with an average size of 500 bp were immunoprecipitated using anti-H3K4me3 (Abcam) or anti-H3K27me3 (Upstate Biotech) antibodies. For all ChIP experiments, quantitative PCR analyses were performed in real-time using the ABI PRISM 7900 sequence detection system and SYBR green master mix as previously described. Relative occupancy values were calculated by determining the apparent immunoprecipitation efficiency (ratios of the amount of immunoprecipitated DNA to that of the input sample) and normalized to the level observed.

Bisulfite Sequencing

Bisulfite treatment of DNA was performed with the Imprint™ DNA Modification Kit (Sigma) according to manufacture's instruction. Amplified products were purified by using gel filtration columns, cloned into the pCR2.1 vector (Invitrogen), and sequenced with M13 forward and reverse primers. Primers that were used for amplifying Nanog promoter had the sequence: 5'-GATTTTGTAGGTGGGAT-TAATTGTGAATTT (SEQ ID NO: 8) and 5'-AC-CAAAAAAACCCACACTCATATCAATATA (SEQ ID NO: 9). Primers that were used for amplifying Oct4 promoter had the sequence: 5'-ATGGGTTGAAATATTGGGTTTATTTA (SEQ ID NO: 10) and 5'-CCACCCTCTAACCTTAAC-CTCTAAC (SEQ ID NO: 11)

Genotyping

PCR amplification was carried out using 500 ng genomic DNA extracted from MEFs, ES cells, iPS cells or embryo yolk sacs for each reaction. The sense primer used for amplifying had the following sequence: 5'-GACGGCATCG-CAGCTTGGATACAC (SEQ ID NO: 1)

Antisense primers used for amplifying had the following sequences.

```
                                      (SEQ ID NO: 2)
     Esrrb: 5'-TGTGGTGGCTGAGGGCATCA (SEQ ID NO: 3)
     Esrra: 5'-TGTAGAGAGGCTCGATGCCCACCAC (SEQ ID NO: 4)
     Esrrg: 5'-GGCAAAGTTCTACCGAATCC (SEQ ID NO: 5)
     Oct4:  5'-CCAATACCTCTGAGCCTGGTCCGAT (SEQ ID NO: 6)
     Sox2:  5'-GCTTCAGCTCCGTCTCCATCATGTT (SEQ ID NO: 7)
     cMyc:  5'-TCGTCGCAGATGAAATAGGGCTG
```

Microarray Analysis mRNAs derived from cells were reverse transcribed, labeled and analyzed using Illumina microarray platform (Sentrix Mouse-6 Expression BeadChip v1.1). Arrays were processed as per manufacturer's instructions. The microarray data were analyzed by SAM.

Generation of Esrrb Reprogrammed Cells

Using direct reprogramming of genetically unmodified fibroblasts as described previously (Blelloch, R., et al., *Cell Stem Cell* (2007) 1, 245-247; Meissner, A., et al., *Nat Biotechnol* (2007) 25, 1177-81). Oct4, Sox2, c-Myc and Esrrb were coexpressed in mouse embryonic fibroblasts (MEFs). The obtained ES cell-like cells were stained positive for alkaline phosphatase, SSEA1 and Nanog (FIG. 2*a-g*). In the following these Oct4, Sox2, c-Myc and Esrrb reprogrammed cells are also referred to as OSCE reprogrammed cells.

Figure 2:
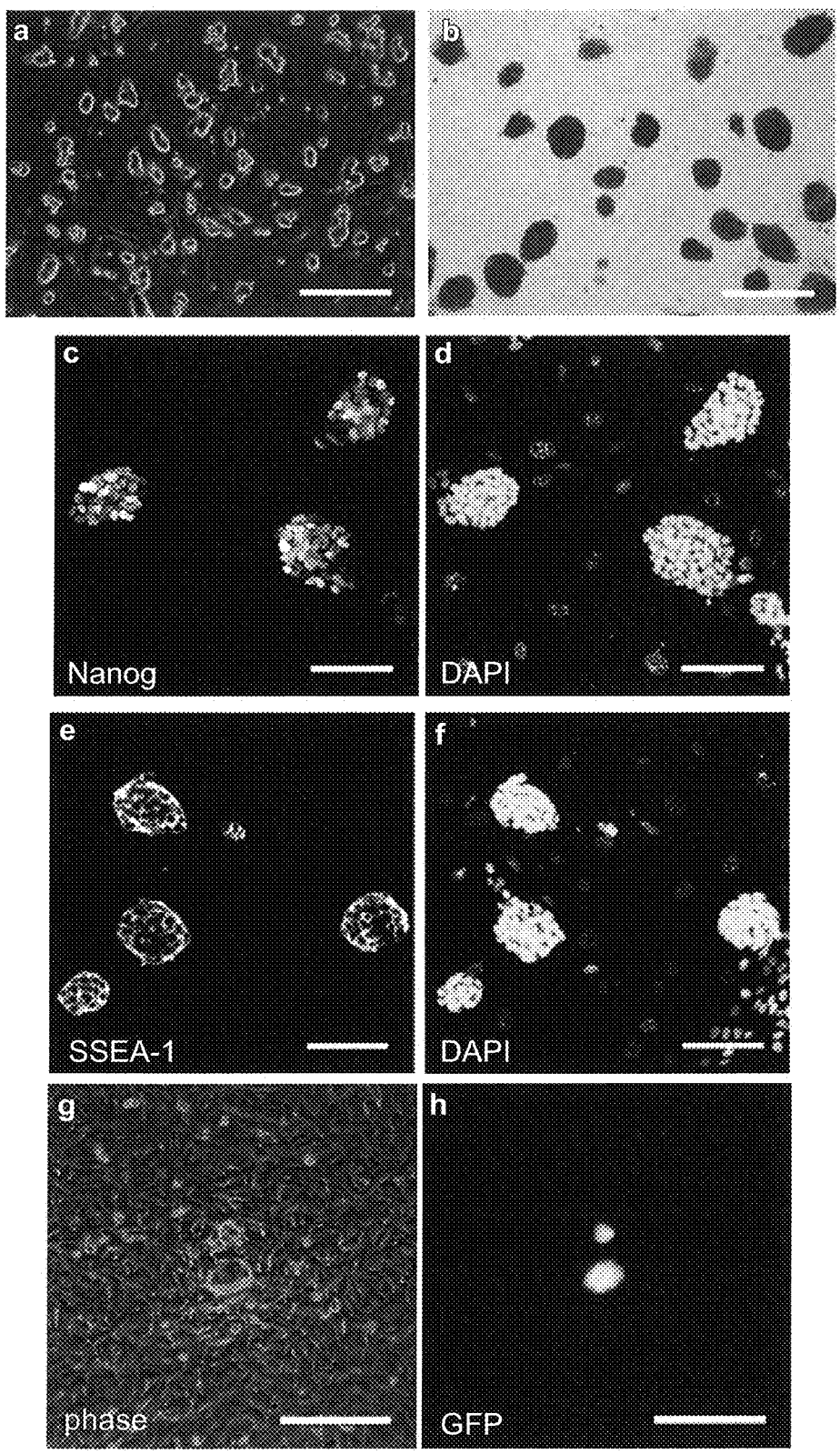
FIG. 2 illustrates Esrrb reprogramming MEF with Oct4, Sox2 and c-Myc. iPS cells recovered from Esrrb, Oct4, Sox2 and c-Myc infected MEF maintained ES-like colonies morphology on feeders (FIG. 2a). Shown is iPS-OSCE clone #13 cultured for 6 passages. Isolated iPS clones stably express ES markers, e.g. alkaline phosphatase (AP) (FIG. 2b), Nanog (FIG. 2c) and SSEA-1 (FIG. 2e). Counterstaining with DAPI in corresponding samples is shown in FIGS. 2d and 2f. In the Pou5fl-GFP MEF, the restoration of endogenous Oct4 indicated by GFP expression was induced by Esrrb, Oct4, Sox2 and c-Myc specifically in iPS colonies, but not in the surrounding fibroblastic cells (FIGS. 2g & 2h). Shown are colonies formed at day 3 after the first passage from a 14 dpi sample.

Consistent with previous reports, Oct4, Sox2 and c-Myc are unable to induce the formation of any stable clones (data not shown; Blelloch, 2007, supra; Nakagawa, 2008, supra). Previous report has demonstrated the use of activation of endogenous Pou5f1 reporter as a stringent selection strategy for the isolation of reprogrammed cells (Wernig et al., 2007, supra). Hence, we used MEFs with Pou5f1-GFP reporter (Szabo, P. E., et al., *Mech Dev* (2002) 115, 157-160) to further verify the potential of Esrrb in inducing ES cell-like colonies with Oct4, Sox2 and cMyc. ES cell-like colonies emerged around 9~11 dpi. We quantified the number of GFP positive colonies on 14 dpi (FIG. 2*h, i*). The efficiency of generation of Esrrb reprogrammed cells was approximately 50% of that obtained by introduction of Klf4, Oct4, Sox2 and c-Myc (FIG. 2j). The result showed that Esrrb can replace Klf4 in reprogramming of MEFs.

Figure 5J:
FIG. 5 illustrates Esrrg reprogramming MEFs in combination with Oct4, Sox2 and c-Myc.
FIG. 5a depicts the reprogramming potential of Esrra and Esrrg. In combination with Oct4, Sox2 and c-Myc, Esrrg induced a number of GFP-positive colonies in Pou5fl-GFP MEFs at 16 dpi. In contrast, Esrra induced only few GFP-positive colonies under the same conditions. A verification of the transcript expression of virus-encoded Esrra, Esrrb and Esrrg in infected MEFs is shown in FIG. 5b. PCR was performed on cDNA using a virus-specific primer and a gene-specific primer.
FIG. 5c depicts reprogrammed cells induced by Esrrg, Oct4, Sox2 and c-Myc from Pou5fl-GFP MEFs. The bright field image is shown. A corresponding fluorescence image to FIG. 5c is shown in FIG. 5d. GFP positive signal indicates that the expression of endogenous Pou5fl gene was restored specifically in the reprogrammed cells, but not in the surrounding fibroblastic cells.
FIG. 5e depicts alkaline phosphatase expression in Esrrg reprogrammed cells.
FIG. 5f depicts Nanog expression in Esrrg reprogrammed cells. To mark nuclei in FIG. 5f cells were stained with Hoechst (FIG. 5g).
FIG. 5h shows the expression of the ES cell specific surface antigen SSEA-1 in Esrrg reprogrammed cells. To mark nuclei in FIG. 5h cells were stained with Hoechst (FIG. 5i). Esrrg reprogrammed cells can differentiate into three major embryonic lineages in EBmediated differentiation (FIG. 5j). The differentiated cells expressed Nestin (neural ectoderm), a-Smooth Muscle Actin (mesoderm) or Gata-4 (endoderm). All lineage markers were stained red and nuclei were counterstained blue with. Hoechst. The chosen cells were generated from Actin-GFP MEFs, with GFP expression indicated by green signals.
FIG. 5k depicts teratotma formation by Esrrg reprogrammed cells. Mallory's tetrachrome staining of sectioned samples showed the differentiation of reprogrammed cells into various tissues derived from all three primary germ layers. Tissues shown correspond to neural ectoderm (ectoderm), blood (mesoderm) and hepatocytes, cells (endoderm). The scale bars represent 100 μm in FIGS. 5c-e, and FIG. 5j; 50 μm in FIGS. 5f-i, and FIG. 5k.
Figure 5K:
Figure 8:
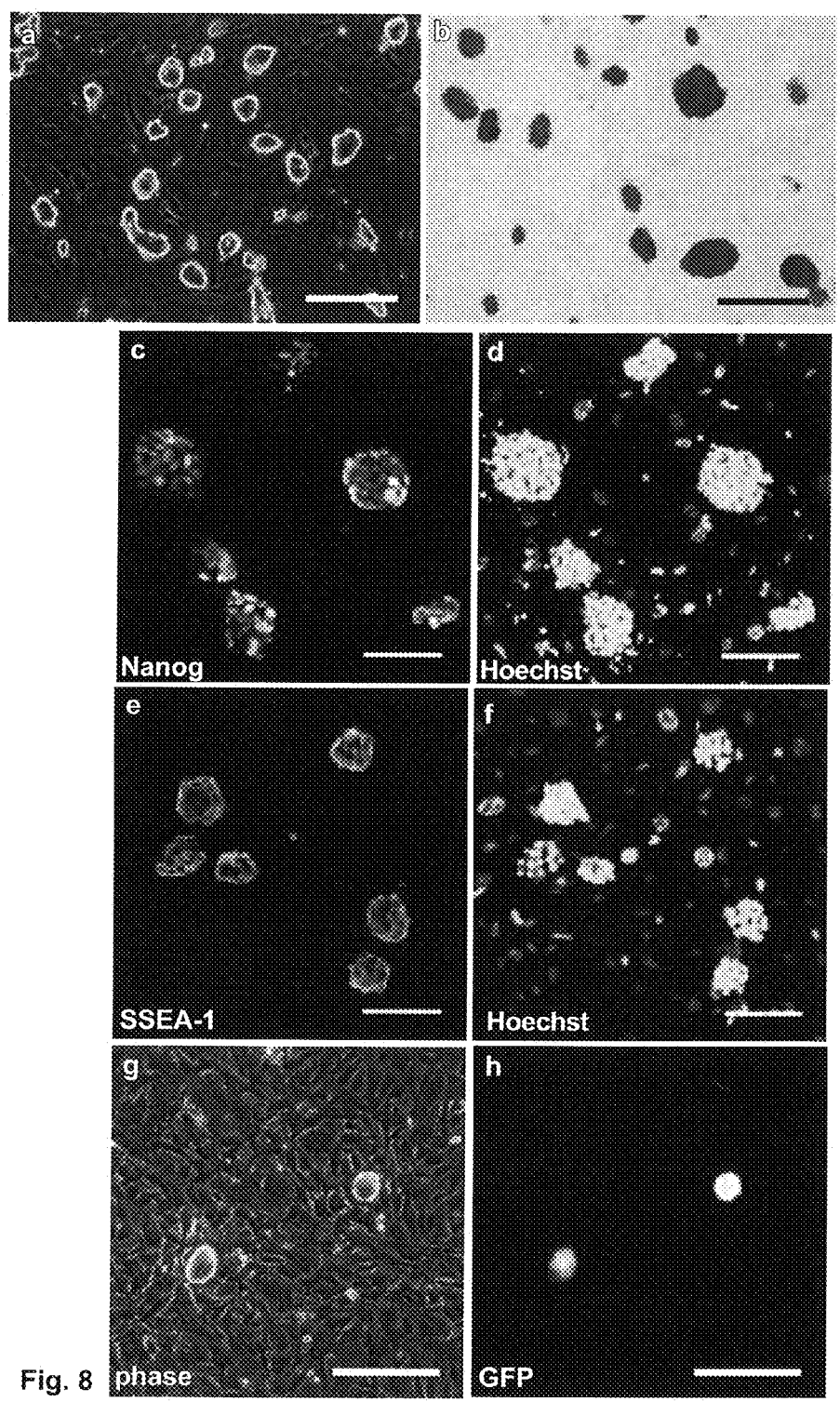
FIG. 8 depicts Esrrb reprogrammed MEF with Oct4 and Sox2, without c-Myc., iPS clones recovered from Esrrb Oct4 and Sox2 infected MEF maintained ES-like morphology on feeders (FIG. 8a), and stably express AP (FIG. 8b), Nanog (FIG. 8c) and SSEA-1 (FIG. 8e).

MEFs were transduced with Pou5f1-GFP reporter with Esrrb, Oct4 and Sox2 and the inventors were able to induce GFP, alkaline phosphatase, Nanog and SSEA1 positive cells (see FIG. 8). MEFs were transduced with Pou5f1-GFP reporter with Esrrg, Oct4, Sox2 and c-Myc and the present inventors were able to induce GFP, alkaline phosphatase, Nanog and SSEA1 positive cells (see FIG. 5).

Characterization of the Reprogrammed Cells

Figure 3B:
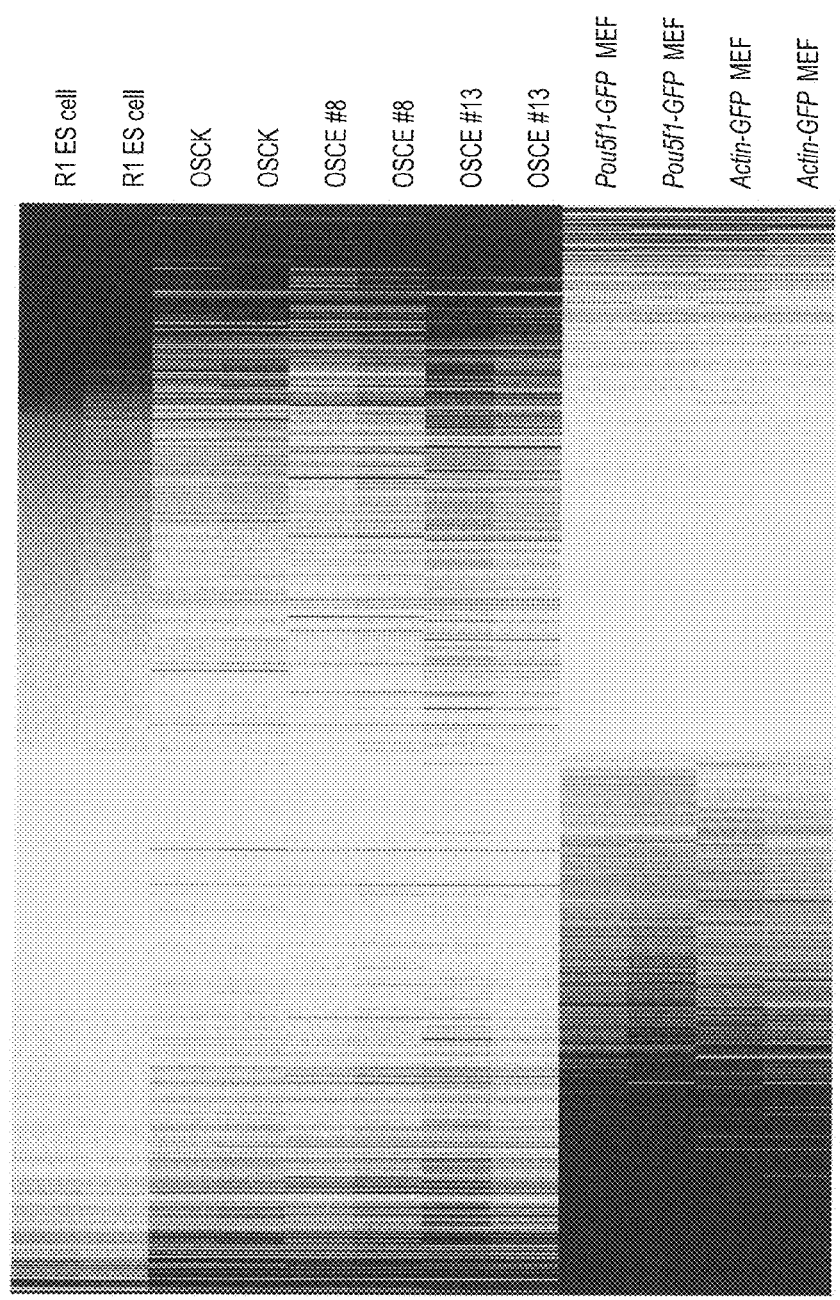
FIG. 3 depicts a global gene-expression analysis of the Esrrb reprogrammed cells. Correlation analysis (46643 transcripts) was performed to cluster gene expression in R1ES cells, reprogrammed cells (OSCE #13 cell-line, OSCE #8 cell-line and OSCK cell-line), Actin-GFP MEF and Pou5fl-GFP MEF (FIG. 3a). OSCK reprogrammed cell-line was obtained by Oct4, Sox2, c-Myc and Klf4. A heatmap in FIG. 3b shows the expression profile of 500 ES cell-associated and MEF-associated genes in the R1ES cells, iPS cells (OSCE #13 reprogrammed cells, OSCE #8 reprogrammed cells and OSCK reprogrammed cells), Actin-GFP MEF and Pou5fl-GFP MEF. The ES cell-associated and MEF-associated genes were selected based on the fold differences of their expression levels between the R1ES cells and the Actin-GFP MEF cells. The genes were sorted by the average expression ratio and mean centered.

To further characterize the Esrrb reprogrammed cells, we performed expression profiling to capture the transcriptome of two ES cell-lines, three reprogrammed cell-lines (two for Esrrb reprogrammed cell-lines and one for Klf4 reprogrammed cell-line) and MEFs derived from two mouse strains. Cluster analysis showed that the reprogrammed cell-lines resembled ES cells more than MEFs (FIG. 3a). Our microarray analysis also revealed the up-regulation of ES cell-associated genes and the down-regulation of MEF-associated genes in the reprogrammed cells (FIG. 3b).

Epigenetic Status of the Reprogrammed Cells

ES cell-specific genes such as Nanog and Pou5f1 are highly expressed in ES cells and their promoter regions are deficient in DNA methylation. In MEFs, these genes are silenced and their promoters acquire DNA methylation. Previous work has shown that reprogramming leads to erasure of DNA methylation (Wernig et al., 2007, supra; Maherali, N., et al., Cell Stem Cell (2007) 1, 55-71; Okita, K., et al., Nature (2007) 448, 313-7). The present inventors assayed the status of DNA methylation at Nanog and Pou5f1 promoters by bisulfite sequencing for ES cells, MEFs and two reprogrammed cell-lines. The result showed that DNA methylation was lost in our reprogrammed cell-lines (FIG. 4a).

Figure 6:
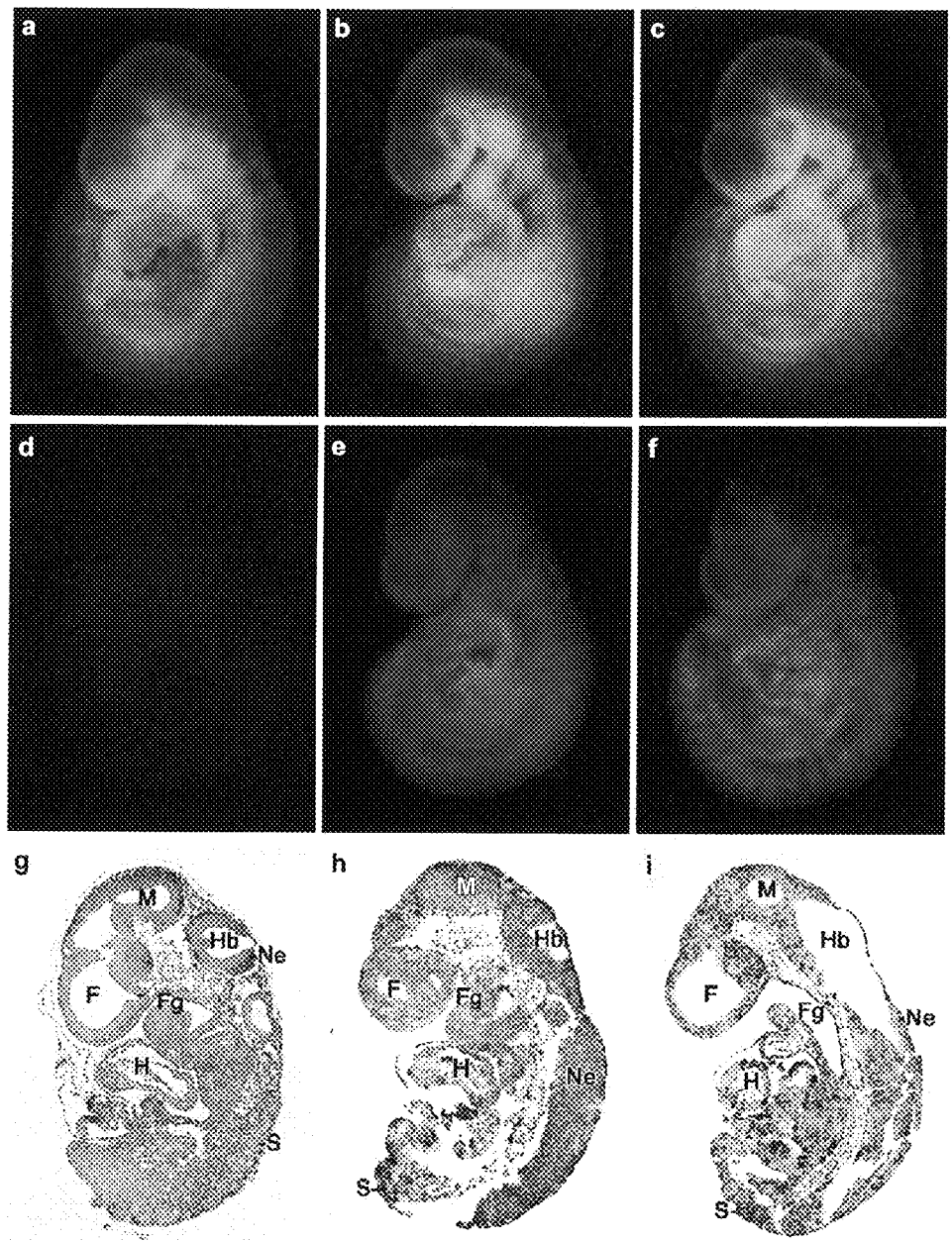
FIG. 6 illustrates that Esrrb reprogrammed cells are pluripotent. Esrrb reprogrammed cells incorporate into mouse embryos and contribute to a broad range of tissues derived from the three major germ layers (FIG. 6a). Two different reprogrammed cells lines were assayed for pluripotent by microinjection into 8-cell stage mouse embryos to generate chimeras, which were collected at E9.5 and observed directly under stero-microscope for EGFP expression.
Figure 9B:
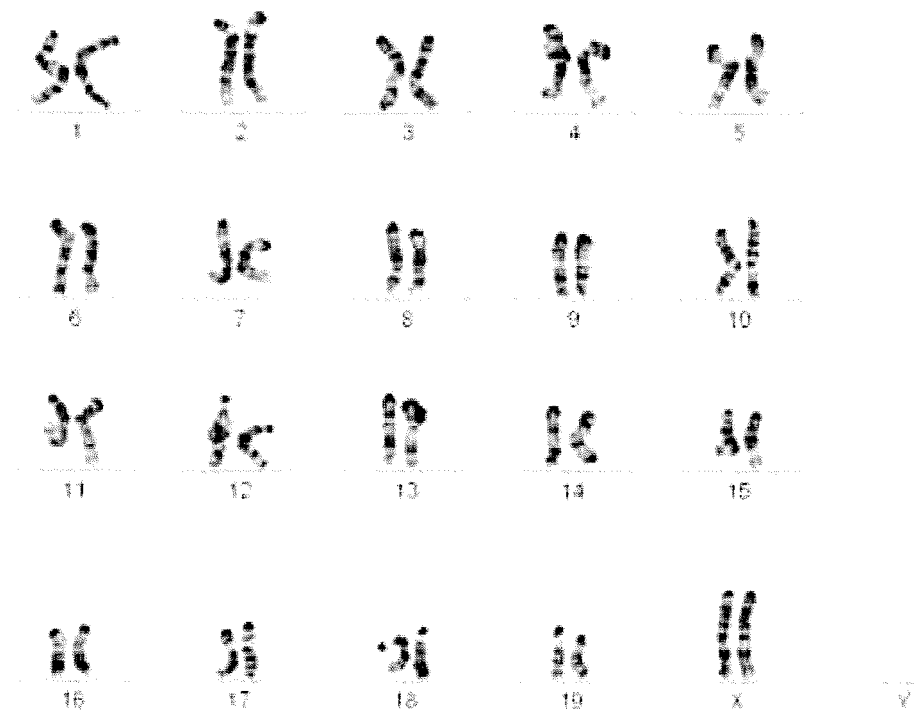
FIGS. 9a and 9b show a normal karyotype for iPS cell lines OSCE#8 (a) and #13 (b). The integration of retroviruses encoding Esrrb, Oct4, Sox2 and c-Myc in the genome was detected using PCR with DNA isolated from iPS cells and yolk sacs of chimera embryos (FIG. 9c-g).
Figure 9C:
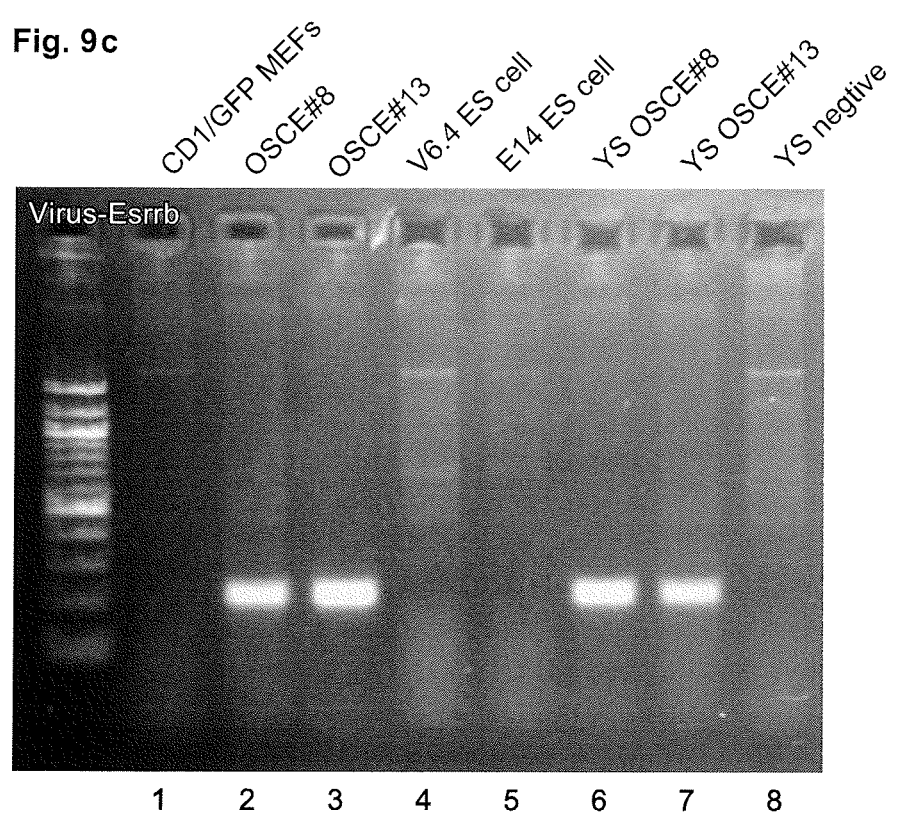
FIG. 9 illustrates the verification of the reprogrammed cell lines induced by Esrrb, Oct4, Sox2 and c-Myc.
Figure 9D:
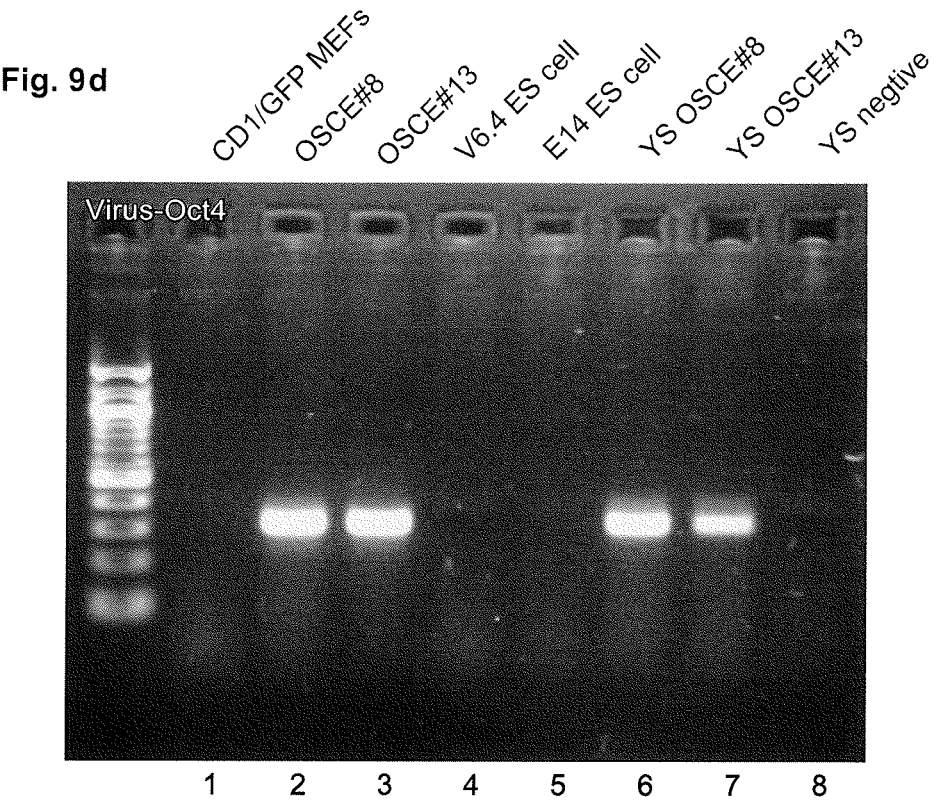
Figure 9E:
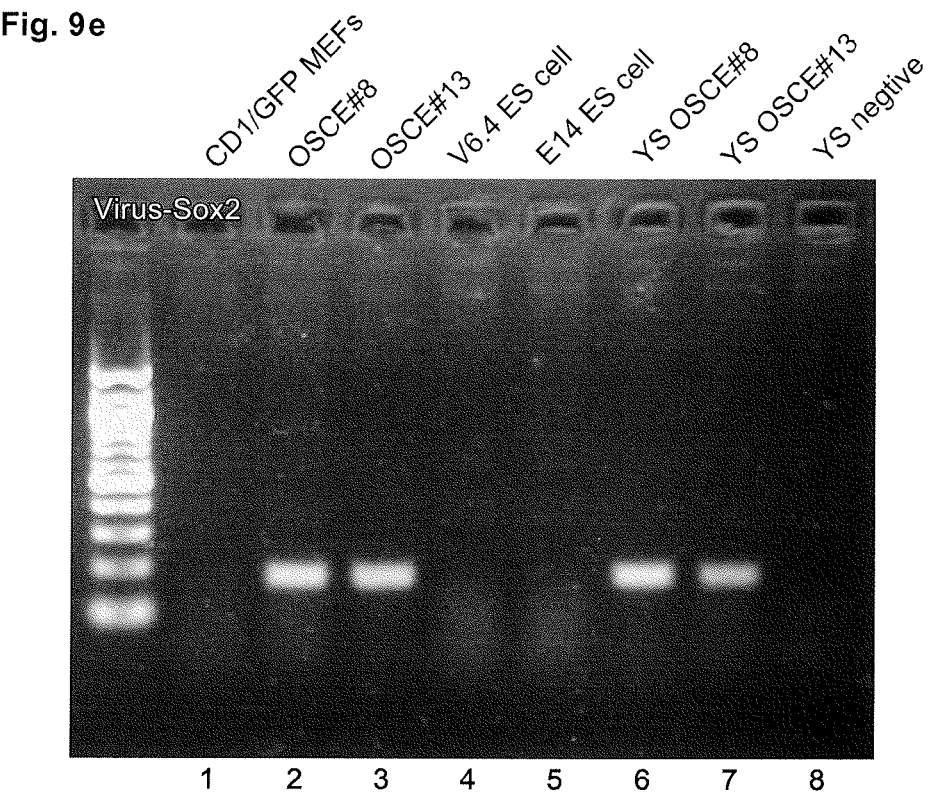
Figure 9F:
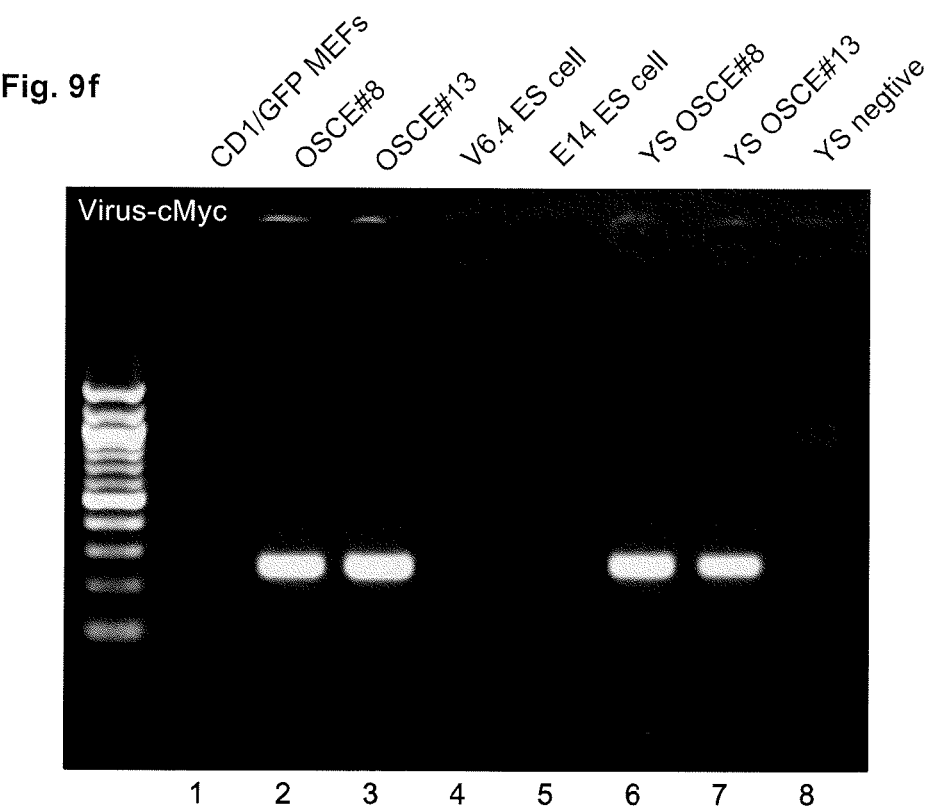
Figure 9G:
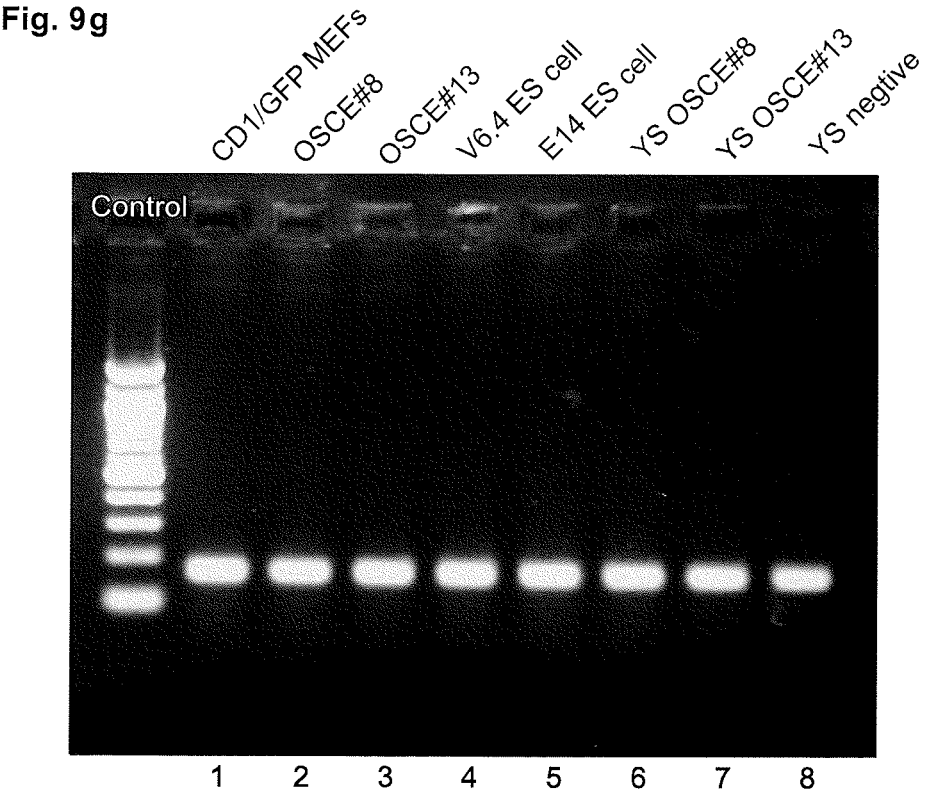
Figure 10A:
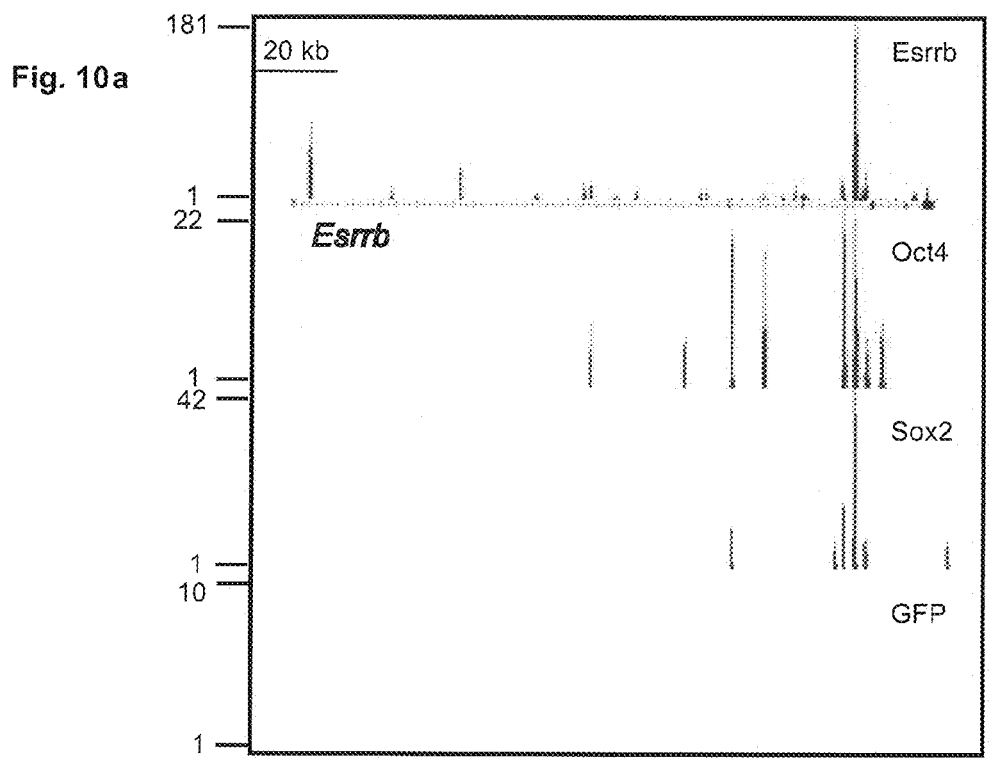
FIG. 10 depicts Esrrb, Oct4 and Sox2 binding profiles in ES cells using the ChIP-seq technology. Screen shots are shown of the T2G browser showing the binding of Esrrb, Oct4, Sox2 and mock ChIP control at Esrrb (FIG. 10a), Klf4 (FIG. 10b), Klf5 (FIG. 10c), Nanog (FIG. 10d), Sall4 (FIG. 10e), Sox2 (FIG. 10f), Tbx3 (FIG. 10g) and Tcl1 (FIG. 10h) gene loci. The cluster density (in green) shows the profile of the binding.
Figure 10B:
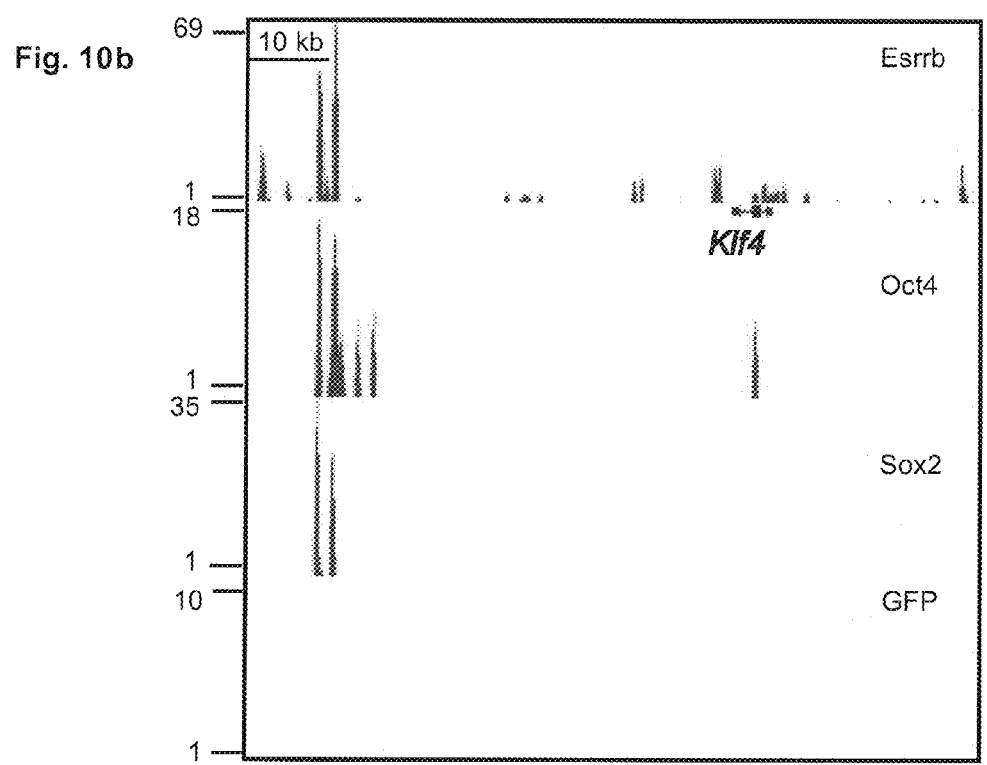
Figure 10C:
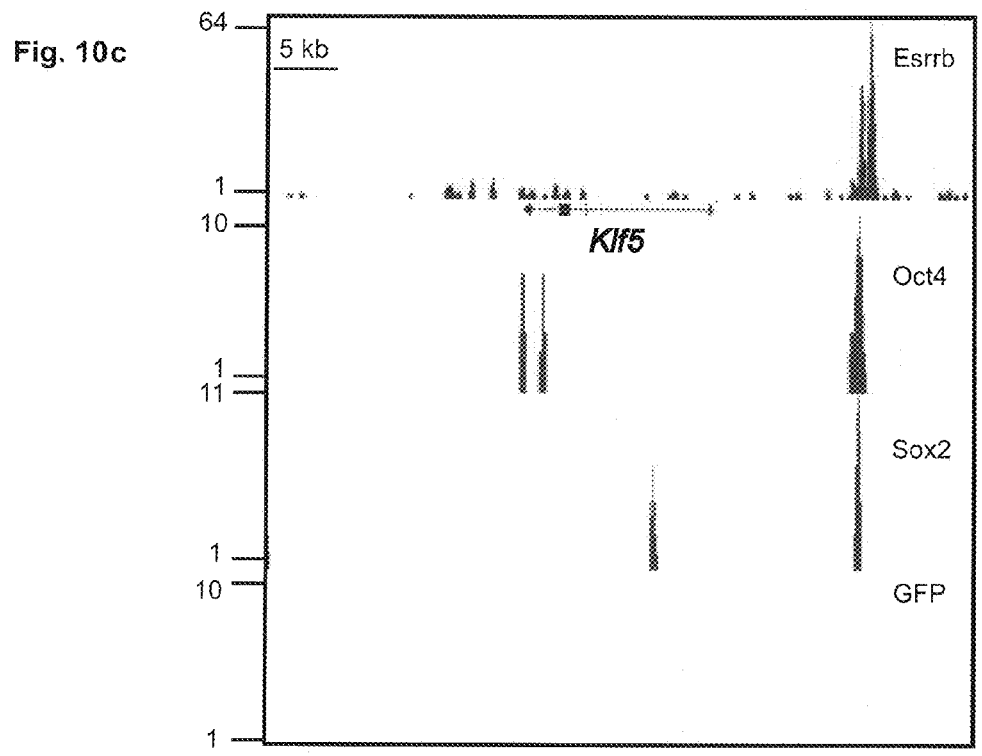
Figure 10D:
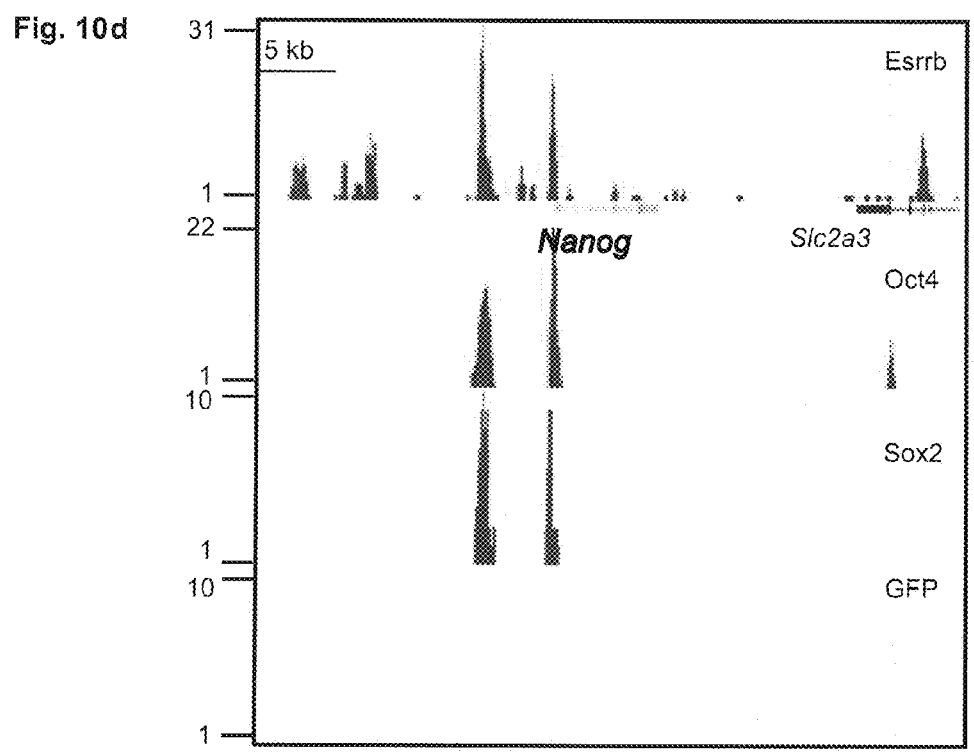
Figure 10G:
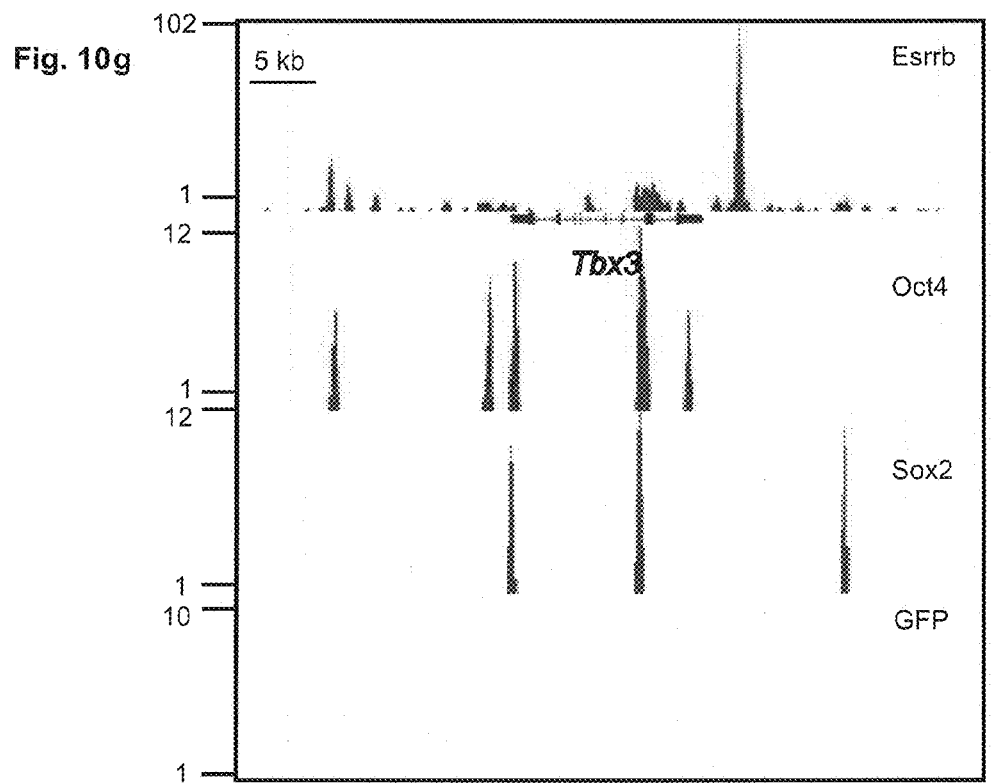
Figure 10H:
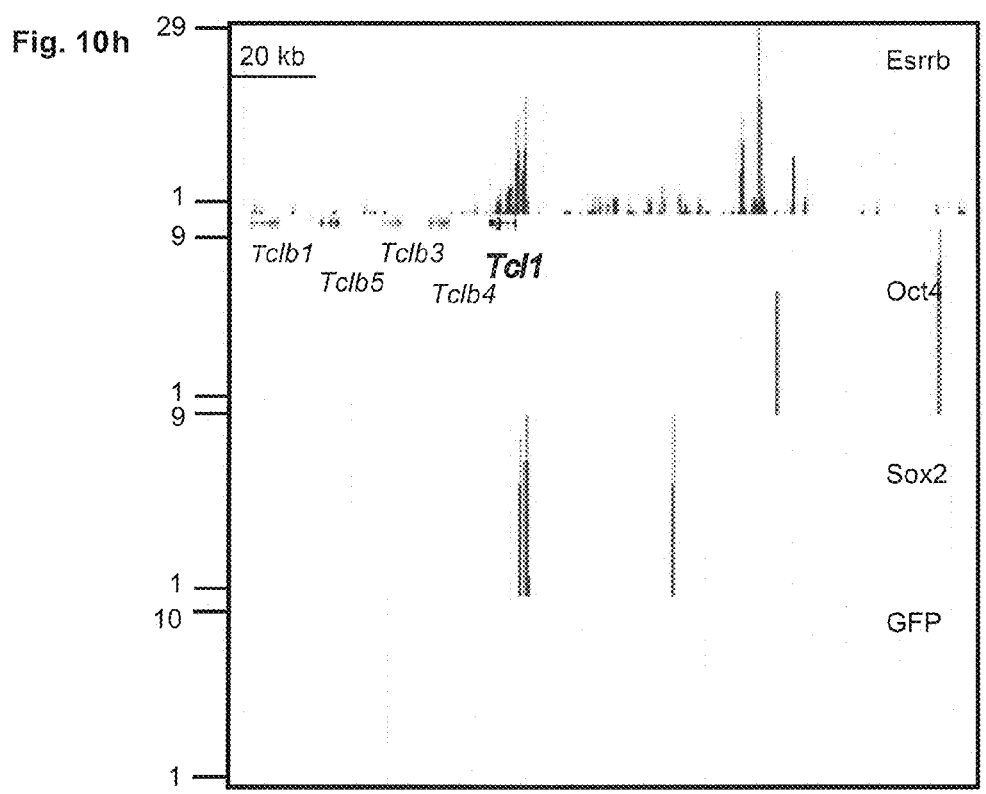

In ES cells, several genes that are repressed but undergo induction when ES cells differentiate exhibit both an active H3K4me3 mark and an inactive H3K27me3 mark (Bernstein, B. E., et al., Cell (2006) 125, 315-326). It was further tested whether these bivalent chromatin structures were present in the Esrrb reprogrammed cells. ChIP assays using anti-H3K4me and anti-H3K27me3 antibodies revealed that the chromatin of seven genes (Zfpm2, NRx2.2, Sox21, Pax5, Lbxlh, Evxl and Dlxl) contained both modifications (FIG. 4b). This result is consistent with previous study demonstrating that bivalent domains are re-formed in iPS cells (Wernig et al., 2007, supra). Altogether, the above data showed that the epigenetic state of the pluripotency genes was reprogrammed from a repressive (methylated) to an active (non-methylated) embryonic state and that bivalent chromatin structures were acquired in the Esrrb reprogrammed cells Esrrb Reprogrammed Cells are Pluripotent To assess if the reprogrammed cells that were obtained are pluripotent, these cells were microinjected into 8 cell stage C57/BL6 embryos. As the OSCE reprogrammed cells were derived from MEFs with actin-GFP reporter, they are GFP positive. Before introducing these cells into the blastocysts, the present inventors first established that the OSCE#8 and OSCE#13 cell-lines had normal karyotype (see FIG. 9a, b). Following injection into blastocysts, the OSCE#8 and OSCE#13 cell-lines contributed to mouse embryos as the 9.5 d.p.c. embryos showed mosaic incorporation of the GFP labeled cells (FIG. 6a-f). The presence of the four retroviruses in the york sac tissues of the chimeric embryos was further confirmed by PCR detection assay (see FIGS. 9c-g). Immunostaining of the embryos also indicated that the GFP-positive cells contributed to all tissues (FIG. 6g-i). Hence, the OSCE reprogrammed cells are pluripotent and able to differentiate in vivo into the three lineages.

Esrrb has been shown to be involved in the maintenance of the self-renewing state of ES cells (Ivanova, N. et al.; Nature (2006) 442, 533-538; Loh, Y. H., et al., Nat. Genet. (2006) 38, 431-440). Thus far, reprogramming factors (Oct4, Sox2, Klf2, Klf4, Klf5, n-Myc and c-Myc) are involved in up-regulating ES cell-specific genes (Ivanova et al., 2006, supra; Loh et al., 2006, supra; Boiani, M. & Scholer, H. R., Nat Rev Mol Cell Biol (2005) 6, 872-884; Cartwright, P., et al., Development (2005) 132, 885-896; Matoba, R., et al., PLoS ONE (2006) 1, e26; Masui, S., et al., Nat. Cell. Biol. (2007) 9, 625-635; Jiang, J., et al., Nat Cell Biol (2008) 10, 353-360). To gain insights into how Esrrb mediates reprogramming with Oct4 and Sox2, the role of Esrrb in regulating gene expression in ES cells was examined. The present inventors have previously mapped the binding sites of Esrrb and other transcription factors in ES cells using the ChIP-seq technology (Chen et al, Cell (2008) 133, 1106-1117). It is of interest to find that Esrrb is bound to intronic sites of the Esrrb gene (see FIG. 10). This suggests that Esrrb could potentially regulate its own expression. Although it is known which genes are bound by Esrrb, it is not clear whether Esrrb is exerting a transcriptional effect on these genes. Therefore, DNA microarray experiments were performed to determine Esrrb bound genes whose expression is reduced upon Esrrb depletion. RNA samples were harvested at different time-points after transfection of shRNA expression constructs. At day 2, the morphology of the ES cells depleted of Esrrb was similar to ES cells transfected with control plasmid expressing shRNA against luciferase (FIG. 6a); these cells also stained positive for alkaline phosphatase. Despite maintaining these ES cell characteristics, the expression of Esrrb bound genes which encode for key regulators of ES cells (Sox2, Nanog, Sall4 Tcl1, Tbx3, Eras, Klf4, Klf5) were already reduced (FIG. 6a). After 4 days and 6 days, the Esrrb depleted ES cells were already differentiated with distinct morphology and loss of alkaline phosphatase staining. The data showed that Esrrb is up-regulating genes associated with ES cell state. As reprogramming of MEFs by Esrrb requires Oct4 and Sox2, genes were identified which are bound Esrrb, Oct4 and Sox2 (FIG. 10). Interestingly, they include genes which encode for regulators of pluripotency (Sox2, Nanog, Sall4), self-renewal regulators (l, Tbx3) and reprogramming factors (Klf4, Klf5) (FIG. 7b). This may provide some explanation as to why Esrrb can work with Oct4 and Sox2 in the reprogramming.

Using affinity purification and mass spectrometry, Esrrb was found in a complex that contained Nanog and Oct4 (Wang et al, 2006, supra; Liang et al., 2008, supra). It is possible that in addition to regulating common target genes, protein-protein interactions between these transcription factors may be important for activating the ES cell-specific gene expression program in somatic cells. It is of interest to test whether other components of the Nanog and Oct4 complexes have reprogramming functions. Previous work on the reprogramming of MEFs to iPS cells highlights a critical role of Klf4 in remodeling cell fate. The above result shows that Klf4 can be replaced by Esrrb. Without being bound by theory the data obtained with ES cells (supra) provide evidence that the three transcription factors Esrrb, Oct4 and Sox2 target common genes which are either critical for maintenance of ES cells or are themselves encoding for reprogramming factors.

The listing or discussion of a previously published document in this specification should not be taken as an acknowledgement that the document is part of the state of the art or is common general knowledge.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Thus, the word "comprise" or variations such as "comprises" or "comprising" will be understood to imply the inclusion of a stated integer or groups of integers but not the exclusion of any other integer or group of integers.

Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

TABLE 1

List of 15 candidate reprogramming factors screened

| Factors | Functions |
|---|---|
| Esrrb | Transcription factor, self-renewal regulator |
| Klf2 | Transcription factor, exhibit redundant function with Klf4 |
| YY1 | Transcription factor |
| E2F2 | Transcription factor |
| Tpt1 | Transcription factor, activator of Oct4 |
| Zfx | Transcription factor, self-renewal regulator |
| Jmjd1a | Epigenetic regulator, histone demethylase |
| Jmjd2c | Epigenetic regulator, histone demethylase |
| Jmjd3 | Epigenetic regulator, histone demethylase |
| Utx | Epigenetic regulator, histone demethylase |
| Gadd45a | Epigenetic regulator, regulator of DNA methylation |
| Gadd45b | Epigenetic regulator, regulator of DNA methylation |
| Gadd45g | Epigenetic regulator, regulator of DNA methylation |
| Eed | Epigenetic regulator, polycomb repressive complex 2 |
| Baf53a | A component of chromatin remodelling complexes |

What is claimed is:

1. A method of reprogramming a cell to produce a cell with pluripotency and self-renewing characteristics, the method comprising increasing the amount or activity of an estrogen-related (Err) protein, or a functional fragments thereof, Oct4, Sox2, and c-Myc in a cultured cell, wherein the cultured cell is a cultured somatic cell, a cultured precursor cell, or a cultured partially differentiated stem cell and wherein the Err protein is one of an Esrrb protein and Esrrg protein.

2. The method of claim 1, wherein the cultured partially differentiated stem cell is one of a lineage-restricted stem cell, a somatic stem cell, and a progenitor cell.

3. The method of claim 1, wherein increasing the amount of Err protein in the cultured cell comprises increasing the expression of the Err protein in the cultured cell.

4. The method of claim 3, wherein increasing the expression of the Err protein in the culture cell comprises increasing expression of a nucleic acid molecule encoding the Err protein in the cultured cell.

5. The method of claim 4, wherein the nucleic acid molecule is heterologous to the cultured cell.

6. The method of claim 4, wherein the nucleic acid molecule is RNA or DNA.

7. The method of claim 1, further comprising assessing one of:
   (i) the amount or the activity of the Err protein, or a functional fragment thereof, in the cell, and
   (ii) the presence of a marker of the differentiation status in the cell.

8. The method of claim 7, wherein the marker of the differentiation status in the cell is: (i) the expression of one of Nanog, Oct4, Sox2, Sall4, Tc11, Tbx3, Eras, Klf2, Klf4, Klf5, Baf250a, BC031441, Eno3, Etv5, Gm1739, Gtf2h3, Hes6, Jub, Mtf2, Myod1, Nmyc1, Notch4, Nr5a2, Nrg2, Otx2, Rab2b, Rbpsuh, Rest, Stat3, Utf1, Tcfap2c, and Zfp553, or (ii) the methylation status of a promoter present in a gene encoding Nanog, Oct4, Sox2, Sall4, Tc11, Tbx3, Eras, Klf2, Klf4, Klf5, Baf250a, BC031441, Eno3, Etv5, Gm1739, Gtf2h3, Hes6, Jub, Mtf2, Myod1, Nmyc1, Notch4, Nr5a2, Nrg2, Otx2, Rab2b, Rbpsuh, Rest, Stat3, Utf1, Tcfap2c, or Zfp553.

9. The method of claim 7, wherein assessing the amount and/or activity of the Err protein comprises assessing the amount and/or activity over a period of time.

10. The method of claim 7, wherein assessing the amount of the Err protein in the cell is achieved by measuring gene expression of the Err protein in the cell.

11. The method of claim 10, further comprising comparing the result of the measurement of Err gene expression with that of a control measurement.

12. The method of claim 11, wherein the control measurement comprises a measurement wherein Err gene expression is not modulated.

13. The method of claim 7, wherein assessing the presence of a marker of the differentiation status in the cell comprises measuring the expression and/or the activity of the marker over a period of time.

14. The method of claim 1, wherein the cell is obtained from an animal.

15. The method of claim 14, wherein the animal is one of a fish, an amphibian, a bird and a mammal.

16. The method of claim 15, wherein the cell is a mammalian somatic cell selected from the group consisting of a fibroblast, a myeloid cell, a B lymphocyte, a T lymphocyte, a dendritic cell, a keratinocyte, an adipose cell, a mesenchymal cell, an epithelial cell, an epidermal cell, a chondrocyte, a hepatocyte, a cumulus cell, a neural cell, a glial cell, an astrocyte, a cardiac cell, an esophageal cell, a muscle cell, a pancreatic beta cell, a melanocyte, a hematopoietic cell, a macrophage, a monocyte, and a mononuclear cell.

17. The method of claim 1, wherein increasing the amount or activity of the Err protein in the cultured cell comprises contacting the cultured cell with a compound that increases the expression or activity of the Err protein.

* * * * *

SEQUENCE LISTING

```
<160> NUMBER OF SEQ ID NOS: 11

<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1
gacggcatcg cagcttggat acac                                            24

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
tgtggtggct gagggcatca                                                 20

<210> SEQ ID NO 3
<211> LENGTH: 25
<212> TYPE: DNA
<213> ORGANISM: Artificial Sequence
<220> FEATURE:
<223> OTHER INFORMATION: Primer

<400> SEQUENCE: 3
tgtagagagg ctcgatgccc accac                                           25

<210> SEQ ID NO 4
<211> LENGTH: 20
<212> TYPE: DNA
<213> ORGANISM: Artificial Sequence
<220> FEATURE:
<223> OTHER INFORMATION: Primer
```

```
<400> SEQUENCE: 4
ggcaaagttc taccgaatcc                                                   20

<210> SEQ ID NO 5
<211> LENGTH: 25
<212> TYPE: DNA
<213> ORGANISM: Artificial Sequence
<220> FEATURE:
<223> OTHER INFORMATION: Primer

<400> SEQUENCE: 5
ccaatacctc tgagcctggt ccgat                                             25

<210> SEQ ID NO 6
<211> LENGTH: 25
<212> TYPE: DNA
<213> ORGANISM: Artificial Sequence
<220> FEATURE:
<223> OTHER INFORMATION: Primer

<400> SEQUENCE: 6
gcttcagctc cgtctccatc atgtt                                             25

<210> SEQ ID NO 7
<211> LENGTH: 23
<212> TYPE: DNA
<213> ORGANISM: Artificial Sequence
<220> FEATURE:
<223> OTHER INFORMATION: Primer

<400> SEQUENCE: 7
tcgtcgcaga tgaaataggg ctg                                               23

<210> SEQ ID NO 8
<211> LENGTH: 30
<212> TYPE: DNA
<213> ORGANISM: Artificial Sequence
<220> FEATURE:
<223> OTHER INFORMATION: Primer

<400> SEQUENCE: 8
gattttgtag ctgggattaa ttgtgaattt                                        30

<210> SEQ ID NO 9
<211> LENGTH: 30
<212> TYPE: DNA
<213> ORGANISM: Artificial Sequence
<220> FEATURE:
<223> OTHER INFORMATION: Primer

<400> SEQUENCE: 9
acaaaaaaaa cccacactca tatcaatata                                        30

<210> SEQ ID NO 10
<211> LENGTH: 26
<212> TYPE: DNA
<213> ORGANISM: Artificial Sequence
<220> FEATURE:
<223> OTHER INFORMATION: Primer

<400> SEQUENCE: 10
atgggttgaa atattgggtt tattta                                            26
```

```
<210> SEQ ID NO 11
<211> LENGTH: 25
<212> TYPE: DNA
<213> ORGANISM: Artificial Sequence
<220> FEATURE:
<223> OTHER INFORMATION: Primer

<400> SEQUENCE: 11
ccaccctcta accttaacct ctaac                                              25
```